US006495321B1

(12) United States Patent
Borrebaeck et al.

(10) Patent No.: US 6,495,321 B1
(45) Date of Patent: *Dec. 17, 2002

(54) METHOD FOR IN VITRO MOLECULAR EVOLUTION OF PROTEIN FUNCTION

(75) Inventors: Carl Arne Krister Borrebaeck, Hjarup; Ulf Hans Eskil Soderlind, S.Sandby; Rebecka Ingrid Camilla Ottosson, Lund, all of (SE)

(73) Assignee: BioInvent International AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/445,649

(22) PCT Filed: Jun. 16, 1998

(86) PCT No.: PCT/GB98/01757

§ 371 (c)(1),
(2), (4) Date: Apr. 6, 2000

(87) PCT Pub. No.: WO98/58080

PCT Pub. Date: Dec. 23, 1998

(30) Foreign Application Priority Data

Jun. 16, 1997 (GB) .............................................. 9712512

(51) Int. Cl.$^7$ ............................. C12Q 1/68; C12P 19/34
(52) U.S. Cl. ............................ 435/6; 435/91.2; 514/44
(58) Field of Search .......................... 435/6, 91.2, 68.1, 435/69.1, 91.1, 199, 810; 530/350; 536/23.1, 24.2, 24.3, 24.33; 514/44

(56) References Cited

U.S. PATENT DOCUMENTS 4,965,188 A 10/1990 Mullis et al.
5,023,171 A 6/1991 Ho et al.

(List continued on next page.)

FOREIGN PATENT DOCUMENTS

EP 0415731 3/1991
EP 0911396 4/1999

(List continued on next page.)

OTHER PUBLICATIONS

Brown. Molecular Biology LabFax. Bios Scientific Publishers. Blackwell Scientific Publications, San Diego, California. pp. 139 and 154, Dec. 1991.*

E.R. Schmidt. Exonuclease digestion of chromosomes for in situ hybridization. Institute of Genetics, Ruhr–University. IRL Press Limited, Oxford England. XP–002082181 p. 10381.

William P.C. Stemmer. Rapid evolution of a protein in vitro by DNA shuffling. Letters to Nature. (Aug. 4, 1994) 370: 389–391.

Andreas Crameri, et al. Molecular evolution of an arsenate detoxification pathway by DNA shuffling. Research XP–002082183. Nature Biotechnology (May 1997) 15:436–438.

(List continued on next page.)

Primary Examiner—Kenneth R. Horlick
(74) Attorney, Agent, or Firm—Dann, Dorfman, Herrell and Skillman

(57) ABSTRACT

The present invention relates to a method for in vitro evolution of protein function. In particular, the method relates to the shuffling of nucleotide segments obtained from exonuclease digestion. The present inventors have shown that polynucleotide fragments derived from a parent polynucleotide sequence digested with an exonuclease can be combined to generate a polynucleofide sequence which encodes for a polypeptide having desired characteristics. This method may be usefully applied to the generation of new antibodies or parts thereof having modified characteristics as compared to the parent antibody.

18 Claims, 9 Drawing Sheets

U.S. PATENT DOCUMENTS

| | | | |
|---|---|---|---|
| 5,043,272 A | | 8/1991 | Hartley |
| 5,252,479 A | | 10/1993 | Srivastava |
| 5,502,167 A | | 3/1996 | Waldmann et al. |
| 5,573,907 A | * | 11/1996 | Carrino et al. ................. 435/6 |
| 5,605,793 A | | 2/1997 | Stemmer |
| 5,714,316 A | | 2/1998 | Weiner et al. |
| 5,811,238 A | | 9/1998 | Stemmer et al. |
| 5,830,721 A | | 11/1998 | Stemmer et al. |
| 5,858,725 A | | 1/1999 | Crowe et al. |
| 6,117,679 A | | 9/2000 | Stemmer |
| 6,132,970 A | | 10/2000 | Stemmer |
| 6,159,690 A | * | 12/2000 | Borrebaeck et al. ........... 435/6 |
| 6,165,793 A | | 12/2000 | Stemmer |
| 6,177,263 B1 | | 1/2001 | Arnold et al. |
| 6,180,406 B1 | | 1/2001 | Stemmer |

FOREIGN PATENT DOCUMENTS

| | | |
|---|---|---|
| EP | 0552266 | 1/2000 |
| WO | 9007936 | 7/1990 |
| WO | 9014430 | 11/1990 |
| WO | 9106570 | 5/1991 |
| WO | 9116427 | 10/1991 |
| WO | 9207075 | 4/1992 |
| WO | 9302191 | 2/1993 |
| WO | 9306213 | 4/1993 |
| WO | 9307282 | 4/1993 |
| WO | 9311237 | 6/1993 |
| WO | 9315208 | 8/1993 |
| WO | 9316192 | 8/1993 |
| WO | 9319172 | 9/1993 |
| WO | 9325237 | 12/1993 |
| WO | 9403596 | 2/1994 |
| WO | 9409817 | 5/1994 |
| WO | 9413804 | 6/1994 |
| WO | 9720078 | 6/1997 |
| WO | 9832845 | 7/1998 |
| WO | 9858080 | 12/1998 |

OTHER PUBLICATIONS

Alber, Tom, et al., "Contributions of hydrogen bonds of Thr 157 to the thermodynamic stability of phage T4 lysozyme." Nature, 330: 41–46 (1987).

Arrizubieta, Maria Jesus and Julio Polaina. "Increased Thermal Resistance and Modification of the Catalytic Properties of a β–Glucosidase by Random Mutagenesis and in Vitro Recombination." The Journal of Biological Chemistry, vol. 275, No. 37: 28843–28848 (2000).

Barbas, III, Carlos F., et al., "Assembly of combinatorial antibody libraries on phages surfaces: The gene III site." Proc. Natl. Acad. Sci., 88: 7978–7982 (1991).

Barbas, III, Carlos F., et al., "Semisynthetic combinatorial antibody libraries: A chemical solution to the diversity problem." Proc. Natl. Acad. Sci., 89: 4457–4461 (1992).

Boder, Eric T. and K. Dane Wittrup, "Yeast surface display for screening combinatorial polypeptide libraries." Nature Biotechnology, 15: 553–557 (1997).

Boublik, Yvan, et al., "Eukaryotic Virus Display: Engineering the Major Surface Glycoprotein of the Autographa californica Nuclear Polyhedrosis Virus (AcNPV) for the Presentation of Foreign Proteins on the Virus Surface." Bio/Technology, 13: 1079–1084 (1995).

"DNA and RNA Modifying Enzymes." (Chapter 5) in Molecular Biology LabFax, ed. T. A. Brown. BIOS Scientific Publishers, Ltd. and Blackwell Scientific Publishers Ltd. (1991).

Buchholz, Christian J., et al., "In vivo selection of protease cleavage sites from retrovirus display libraries." Nature Biotechnology, 16: 951–954 (1998).

Chang, Chia–Chun J., et al., "Evolution of a cytokine using DNA family shuffling." Nature Biotechnology, 17: 793–797 (1999).

Christians, Fred C., et al., "Directed evolution of thymidine kinase for AZT phosphorylation using DNA family shuffling." Nature Biotechnology, 17: 259–264 (1999).

Crameri, Andreas and Willem P.C. Stemmer, "Combinatorial Multiple Cassette Mutagenesis Creates All the Permutations of Mutant and Wild–Type Sequences." BioTechniques, vol. 18, No. 2: 194–196 (1995).

Crameri, Andreas, et al., "DNA shuffling of a family of genes from diverse species accelerates directed evolution." Nature, 391: 288–291 (1998).

Crameri, Andreas, et al., "Molecular evolution of an arsenate detoxification pathway by DNA shuffling." Nature Biotechnology, 15: 436–438 (1997).

Dower, William J., et al., "High efficiency transformation of E. coli by high voltage electroporation." Nucleic Acids Research, vol. 16, No. 13: 6127–6145 (1988).

Eckstein, Fritz. "Exogenous application of ribozymes for inhibiting gene expression." Ciba Foundation Symposium, 207–217 (1997).

Ernst, Wolfgang, et al., "Baculovirus surface display: construction and screening of a eukaryotic epitope library." Nucleic Acids Research, vol. 26, No. 7: 1718–1723 (1998).

Fisch, Igor, et al., "A strategy of exon shuffling for making large peptide repertoires displayed on filamentous bacteriophage." Proc. Natl. Acad. Sci., 93: 7761–7766 (1996).

Grabherr, R., et al., "Expression of Foreign Proteins on the Surface of Autographa Californica Nuclear Polyhedrosis Virus." BioTechniques, 22: 730–735 (1997).

Granziero, Luisa, et al., "Baculovirus cDNA libraries for expression cloning of genes encoding cell–surface antigens." Journal of Immunological Methods, 203: 131–139 (1997).

Grifiths, Andrew D., et al., "Isolation of high affinity human antibodies directly from large synthetic repertoires." Journal of Embo., 13(14): 3245–3260 (1994).

Kikuchi, Miho, et al., "An effective family shuffling method using single–stranded DNA." Gene, 243: 133–137 (2000).

Kim, Yong–Sung, et al., "Bacterial Cell Surface Display of an Enzyme Library for Selective Screening of Improved Cellulase Variants." Applied and Environmental Microbiology, vol. 66, No. 2: 788–793 (2000).

Kuipers, Oscar P., et al., "Improved site–directed mutagenesis method using PCR." Nucleic Acids Research, vol. 19, No. 16: 4558 (1991).

Larrick, James W., et al., "Rapid cloning of rearranged immunoglobulin genes from human hybridoma cells using mixed primers and the polymerase chain reaction." Biochemical and Biophysical Research Communications, vol. 160, No. 3: 1250–1256 (1989).

Leung, David W., et al., "A method for random mutagenesis of a defined DNA segment using a modified polymerase chain reaction." Technique–A Journal of Methods in Cell and Molecular Biology, vol. 1, No. 1: 11–15 (1989).

Hanahan, Douglas., "Studies on Transformation of Escherichia coli with Plasmids." J. Mol. Biol., 166: 557–580 (1983).

Higuchi, Kazuo, et al., "Cell display library for gene cloning of variable regions of human antibodies to hepatitis B surface antigen." Journal of Immunological Methods, 202: 193–204 (1997).

Huse, William D., et al., "Generation of a Large Combinatorial Library of the Immunoglobulin Repertoire in Phage Lambda." Science, 246: 1275–1281 (1989).

Mottershead, David, et al., "Baculoviral Display of the Green Fluorescent Protein and Rubella Virus Envelope Proteins." Biochemical and Biophysical Communications, 238: 717–722 (1997).

McCafferty, John, et al., "Phage antibodies: filamentous phage displaying antibody variable domains." Nature, 348: 552–554 (1990).

Marks, James D., et al., "By–Passing Immunization: Building High Affinity Human Antibodies by Chain Shuffling." Bio/Technology, 10: 779–783 (1992).

Lu, Tao and Horace B. Gray Jr., "Kinetics and mechanism of BAL 31 nuclease action on small substrates and single–stranded DNA." Biochimica et Biophysica Acta, 1251: 125–138 (1995).

Ostermeier, Marc, et al., "A combinatorial approach to hybrid enzymes independent of DNA homology." Nature Biotechnology, 17: 1205–1209 (1999).

Parmley, Stephen F. and George P. Smith, "Antibody–selectable filamentous fd phage vectors: affinity purification of target genes." Gene, 73: 305–318 (1988).

Schier, Robert, et al., "Isolation of Picomolar Affinity Anti––c–erbB–2 Single–chain Fv by Molecular Evolution of the Complementarity Determining Regions in the Center of the Antibody Binding Site." J. Mol. Biol., 263: 551–567 (1996).

Schmidt, E. R., "Exonuclease digestion of chromosomes for in situ hybridization." Nucleic Acids Res., 16(21): 10381 (1988).

Sock, Elisabeth, et al., "DNA Replication of Human Polyomavirus JC is Stimulated by NF–I in Vivo." Virology, 182: 298–308 (1991).

Stemmer, Willem P. C., "Rapid evolution of a protein In Vitro by DNA shuffling." Nature, 370: 389–391 (1994).

Stemmer, Willem P. C., "DNA shuffling by random fragmentation and reassembly: In Vitro recombination for molecular evolution." Proc. Natl. Acad. Sci., 91: 10747–10751 (1994).

Vaish, Narendra K., et al., "In vitro selection of a purine nucleotide–specific hammerhead–like ribozyme." Proc. Natl. Acad. Sci., 95: 2158–2162 (1998).

Warren, Mark S., et al., "A Rapid Screen of Active Site Mutants in Glycinamide Ribonucleotide Transformylase." Biochemistry, 35: 8855–8862 (1996).

Yang, Wei–Ping, et al., "CDR Walking Mutagenesis for the Affinity Maturation of a Potent Human Anti–HIV–1 Antibody into the Picomolar Range." J. Mol. Biol., 254: 392–403 (1995).

Zhang, Ji–Hu, et al., "Directed evolution of a fucosidase from a galactosidase by DNA shuffling and screening." Proc. Natl. Acad. Sci., 94: 4504–4509 (1997).

Paabo, Svante, "Amplifying Ancient DNA." (Chapter 20) in PCR Protocols: A Guide to Methods and Applications. Academic Press, Inc. (1990).

Frank, Ronald, et al., "Simultaneous Synthesis and Biological Applications of DNA Fragments: An Efficient and Complete Methodology." Methods in Enzymology, 154: 221–249 (1987).

Deng, Su–jun, et al., "Simultaneous randomization of antibody CDRs by a synthetic ligase chain reaction strategy." Nucleic Acids Research, vol. 21, No. 18:4418–4419 (1993).

Meyerhans, Andreas, et al., "DNA recombination during PCR." Nucleic Acids Research, 18(7): 1687–1691 (1990).

Yolov, A. A. and Z. A. Shabarova, "Constructing DNA by polymerase recombination." Nucleic Acids Research, vol. 18, No. 3: 3983–3986 (1990).

Klug, Jorg, et al., "Creating chimeric molecules by PCR directed homologous DNA recombination." Nucleic Acids Research, vol. 19, No. 10: 2793 (1991).

Saiki, Randall K., et al., "Primer–Directed Enzymatic Amplification of DNA with a Thermostable DNA Polymerase." Science, 239: 487–491 (1988).

Daugherty, Bruce L., et al., "Polymerase chain reaction facilities the cloning, CDR–grafting, and rapid expression of a murine monoclonal antibody directed against the CD18 component of leukocyte integrins." Nucleic Acids Research, vol. 19, No. 9: 2471–2476 (1991).

Krishnan, B. Rajendra, et al., "Direct and crossover PCR amplification to facilitate Tn5supF–based sequencing of λ phage clones." Nucleic Acids Research, vol. 19, No. 22: 6177–6182 (1991).

Majumder, Kamud, "Ligation–free gene synthesis by PCR: synthesis and mutagenesis at multiple loci of a chimeric gene encoding OmpA signal peptide and hirudin." Gene, 110: 89–94 (1992).

Heda, Ghanshyam D., et al., "A simple in vitro site directed mutagenesis of concatamerized cDNA by inverse polymerase chain reaction." Nucleic Acids Research, vol. 20, No. 19: 5241–5242 (1992).

Osuna, Joel, et al., "Combinatorial mutagenesis of three major groove–contacting residues of EcoRI: single and double amino acid replacements retaining methyltransferase–sensitive activities." Gene, 106: 7–12 (1991).

Jones, Douglas H. and Stanley C. Winistorfer, "Recombinant Circle PCR and Recombination PCR for Site–Specific Mutagenesis Without PCR Product Purification." BioTechniques, vol. 12, No. 4: 528–534 (1992).

Osuna, Joel, et al., "Microbial Systems and Directed Evolution of Protein Activities." Critical Reviews in Microbiology, 20(2): 107–116 (1994).

Shuldiner, Alan R., et al., "Hybrid DNA artifact from PCR a closely related target sequences." Nucleic Acids Research, vol. 17, No. 11: 4409 (1989).

Gram, Hermann, et al., "In vitro selection and affinity maturation of antibodies from a naive combinatorial immunoglobulin library." Proc. Natl. Acad. Sci., 89: 3576–3580 (1992).

Paabo, Svante, et al., "Acient DNA and the Polymerase Chain Reaction." The Journal of Biological Chemistry, 264(17): 9709–9712 (1989).

Jansen, Ruud and Fred D. Ledley, "Disruption of phase during PCR amplification and cloning of heterozygous target sequences." Nucleic Acids Research, 18(17): 5153–5156 (1990).

Paabo, Svante, et al., "DNA Damage Promotes Jumping between Templates during Enzymatic Amplification." The Journal of Biological Chemistry, 265(8): 4718–4721 (1990).

Lewis, Alan P. and J. Scott Crowe, "Immunoglobulin complementarity–determining region grafting by recombinant polymerase chain reaction to generate humanised monoclonal antibodies." Gene, 101: 297–302 (1991).

Goloubinoff, Pierre, et al., "Evolution of maize inferred from sequence diversity of an Adh2 gene segment from archaelogical specimens." Proc. Natl. Acad. Sci., 90: 1997–2001 (1993).

Vallette, Francois, et al., "Construction of mutant and chimeric genes using the polymerase chain reaction." Nucleic Acids Research, 17(2): 723–733 (1988).

Sarkar, Gobinda and Steve S. Sommer, "The 'Megaprimer' Method of Site–Directed Mutagenesis." BioTechniques, 8(4): 404–407 (1990).

Higuchi, Russell, et al., "A general method of in vitro preparation and specific mutagenesis of DNA fragments: study of protein and DNA interactions." Nucleic Acids Research, 16: 7351–7367 (1988).

Innis, Michael A., et al., "PCR Protocols a Guide to Methods and Applications." Academic Press, Inc. (1990).

Higuchi, Russell, "Recombinant PCR." (Chapter 22) in PCR Protocols: A Guide to Methods and Applications. Academic Press, Inc. (1990).

Frohman, Michael A. and Gali R. Martin, "Detection of Homologous Recombinants." (Chapter 28) in PCR Protocols: A Guide to Methods and Applications. Academic Press, Inc. (1990).

Marks, James D., et al., "By–passing Immunization: Human Antibodies from V–gene Libraries Displayed on Phage." J. Mol. Biol., 222: 581–597 (1991).

Nassal, Michael and Andrea Rieger, "PCR–based site–directed mutagenesis using primers with mismatched 3'–ends." Nucleic Acids Research, 18(10): 3077–3078 (1990).

Landt, Olfert, et al., "A general method for rapid site–directed mutagenesis using the polymerase chain reaction." Gene, 96: 125–128 (1990).

Berger, Shelby L., et al., "Phoenix Mutagenesis: One–Step Reassembly of Multiply Cleaved Plasmids with Mixtures of Mutant and Wild–Type Fragments." Analytical Biochemistry, 214: 571–579 (1993).

Yon, Jeff and Mike Fried, "Precise gene fusion by PCR." Nucleic Acids Research, 17(12): 4895 (1989).

Horton, Robert M., et al., "Gene Splicing by Overlap Extension: Tailor–Made Genes Using the Polymerase Chain Reaction." BioTechniques, 8(5): 528–535 (1990).

Horton, Robert M., et al., "Gene Splicing by Overlap Extension." Methods in Enzymology, 217: 270–279 (1993).

Smith, Kelly D., et al., "Unwanted Mutations in PCR Mutagenesis: Avoiding the Predicatble." PCR Methods and Applications, 2: 253–257 (1993).

Brakenhoff, Ruud H., et al., "Chimeric cDNA clones: a novel PCR artifact." Nucleic Acids Research, 19(8): 1949 (1991).

Horton, Robert M., et al., "Engineering hybrid genes without the use of restriction enzymes: gene splicing by overlap extension." Gene, 77: 61–68 (1989).

Marton, Attila, et al., "DNA nicking favors PCR recombination." Nucleic Acids Research, 19(9): 2423–2426 (1991).

Ho, Steffan N., et al., "Site–directed mutagenesis by overlap extension using the polymerase chain reaction." Gene, 77: 51–59 (1989).

* cited by examiner

Figure 6A

CTAGCGCTATATGCGTTGATGCAATTTCTATGAGCACCCGTTCTCGGAGCACTGTCC
GACCGCTTTGGCCGCCGCCCAGTCCTGCTCGCTTCGCTACTTGGAGCCACTATCGAC
TACGCGATCATGGCGACCACACCCGTCCTGTGGATCCTCTACGCCGGACGCATCGTG
GCCGGCATCACCGGCGCCACAGGTGCGGTTGCTGGCGCCTATATCGCCGACATCACC
GATGGGGAAGATCGGGCTCGCCACTTCGGGCTCATGAGCGCTTGTTTCGGCGTGGGT
ATGGTGGCAGGCCCCGTGGCCGGGGGACTGTTGGGCGCCATCTCCTTGCATGCACCA
TTCCTTGCGGCGGCGGTGCTCAACGGCCTCAACCTACTACTGGGCTGCTTCCTAATG
CAGGAGTCGCATAAGGGAGAGCGTCGACCGATGCCCTTGAGAGCCTTCAACCCAGTC
AGCTCCTTCCGGTGGGCGCGGGGCATGACTATCGTCGCCGCACTTATGACTGTCTTC
TTTATCATGCAACTCGTAGGACAGGTGCCGGCAGCGCTCTGGGTCATTTTCGGCGAG
GACCGCTTTCGCTGGAGCGCGACGATGATCGGCCTGTCGCTTGCGGTATTCGGAATC
TTGCACGCCCTCGCTCAAGCCTTCGTCACTGGTCCCGCCACCAAACGTTTCGGCGAG
AAGCAGGCCATTATCGCCGGCATGGC

Figure 6B

GAGCCACTATCGACTACGCGATCATGGCGACCACACCCGTCCTGTGGATCCTCTACG
CCGGACGCATCGTGGCCGGCATCACCGGCGCCACAGGTGCGGTTGCTGGCGCCTATA
TCGCCGACATCACCGATGGGGAAGATCGGGCTCGCCACTTCGGGCTCATGAGCGCTT
GTTTCGGCGTGGGTATGGTGGCAGGCCCCGTGGCCGGGGGACTGTTGGGCGCCATCT
CCTTGCATGCACCATTCCTTGCGGCGGCGGTGCTCAACGGCCTCAACCTACTACTGG
GCTGATTCCTAATGCAGGAGTCGCATAAGGGAGAGCG

Figure 7A

CCGTTNAAGNNNACACAGTTANATTGTTAANGCAGTCAGGCACCGTGTATGAAATC
TAACAATGCGCTCATCGTCATCCTCGGNACCGTCACCCTGGATGTTGTAGGCATAG
GCTTGGTTATGCCGGTACTGCCGGGCCTCTTGCGGGATATCGTCCATTCCGACAGN
ATCGCCAGTCACTATGGNGTGCTGCTAGCGCTATATGCGTTGATGCAATTTCTATG
AGCACCCGTTCTCGGAGCACTGTCCGACCGCTTTGGCCGCCGCCCAGTCCTGCTCG
CTTCGCTACTTGGAGCCACTATCGACTACGCGATCATGGCGACCACACCCGTCCTG
TGGATCCTCTACGCCGGACGAATCGATGGCCGGAATCACCGGGGTCACAGGTGCG
GNTGCTGGNGCCTATTTCGCCGACATCAACGATGGGGAAAGATCNGGCTCGNCAC
TNCGGGCTCATNAGNNTTTGGTTTCGGCNTGGGTATTGGTNGGAAGNCCCCCANG
GCCGGGGGGATTGTTNGNGNGCCAACTTCCTTGGATTGAACAATNCCCTNGGGGG
GGGGGGGTTCANCNGGCNCAACCTATTNNTGGGATTNTTNCNNATNNAGAGTCGA
TAAGGAGGNGNNGGCCANTCCNTGNAGCCCACCC

Figure 7B

CAGTATGACCATNNNCTAGCTTCTCGNCGAGACGTTTGGTNGCNGGACCAGTTAC
GAAGGCTTGAGCNAGGGAGTTGAAGATTCCNTATACTNAATGNGATAGGNCTATC
ATCGGNGGGCTCCANAGATAGCGGNCANCGNCNACANATGACCCAGAGCTNTGC
CGGCANCAGTCCTACGAGTNGNATGATNAAGTAGANAGGCATAATTGGGGNGACG
ATAGTCATGNCCCGCGGCCACCGGAAGGAGCTTAATGGGTTGNNGGCTCTCAAGG
GCATCGGTCGACGCTCTCCCTTATGTGACTCNTGNATTAGGAATCAGCCCAGTTNG
CTAGGTTTGNGGCCGNTTGNAANCAACCCCCGNCCNNANAGGGAATTGNTGNAAT
NNAAAGGGNGTTTGGGNGNCCCAACAAGTCCCCCCCGNGCNANNGGGGGCCCTC
CCACCAATTNCCCCACGGCCGAAAAAAAANGTTTTCAATNAAGCCCCNAGGTNGG
GGAACCCCTNTTCTTCCCCCATCGGNGGANATTGGNTGAATTTTTGGGGNCCAAN
ANNCCCNNCTTTNGGGTCCGNTNTTATNTCCCNCCCACAATTNNTTCCCGTTTNGG
GGNNNNNTCCNAANGAAGGTTTTNTTTCCCCCCCNATTTCCNCTTTATNCNNTTTN
TNNTTTNNNNATAGAAAAANAAAANTTTGGGGGNGCCAAGGTTTNATAATATTT

```
AAGCTTGCATGCAAATTCTATTTCAAGGAGACAGTCATAATGAAATACCTATTGCCTACGGC
AGCCGCTGGATTGTTATTACTCGCGGCCCAACCGGCCATGGCATGAGCGGCCGCCCGGGCGG
CGCGCCCTGCAGGCTAGCACTAGTGGTACCGTCGACAAGAAAGTTGAGCCCAAATCTTCAAC
TAAGACGCACACATCAGGAGGTTAGGGTGGCGGTGGCTCTCCATTCGTTTGTGAATATCAAG
GCCAATCGTCTGACCTGCCTCAACCTCCTGTCAATGCTGGCGGCGGCTCTGGTGGTGGTTCT
GGTGGCGGCTCTGAGGGTGGTGGCTCTGAGGGTGGCGGTTCTGAGGGTGGCGGCTCTGAGGG
AGGCGGTTCCGGTGGTGGCTCTGGTTCCGGTGATTTTGATTATGAAAAGATGGCAAACGCTA
ATAAGGGGGCTATGACCGAAAATGCCGATGAAACGCGCTACAGTCTGACGCTAAAGGCAAA
CTTGATTCTGTCGCTACTGATTACGGTGCTGCTATCGATGGTTTCATTGGTGACGTTTCCGG
CCTTGCTAATGGTAATGGTGCTACTGGTGATTTGCTGGCTCTAATTCCCAAATGGCTCAAG
TCGGTGACGGTGATAATTCACCTTTAATGAATAATTTCCGTCAATATTTACCTTCCCTCCCT
CAATCGGTTGAATGTCGCCCTTTTGTCTTTAGCGCTGGTAAACCATATGAATTTTCTATTGA
TTGTGACAAAATAAACTTATTCCGTGGTGTCTTTGCGTTTCTTTTATATGTTGCCACCTTTA
TGTATGTATTTTCTACGTTTGCTAACATACTGCGTAATAAGGAGTCTTAATAAGGGAGCTTG
CATGCAAATTCTATTTCAAGGAGACAGTCATAATGAAATACCTATTGCCTACGGCAGCCGCT
GGATTGTTATTACTGAATTCACTGGCCGTCGTTTTACAACGTCGTGACTGGGAAAACCCTGG
CGTTACCCAACTTAATCGCCTTGCAGCACATCCCCCTTTCGCCAGCTGGCGTAATAGCGAAG
AGGCCCGCACCGATCGCCCTTCCCAACAGTTGCGCAGCCTGAATGGCGAATGGCGCCTGATG
CGGTATTTTCTCCTTACGCATCTGTGCGGTATTTCACACCGCATACGTCAAAGCAACCATAG
TACGCGCCCTGTAGCGGCGCATTAAGCGCGGCGGGTGTGGTGGTTACGCGCAGCGTGACCGC
TACACTTGCCAGCGCCCTAGCGCCCGCTCCTTTCGCTTTCTTCCCTTCCTTTCTCGCCACGT
TCGCCGGCTTTCCCCGTCAAGCTCTAAATCGGGGGCTCCCTTTAGGGTTCCGATTTAGTGCT
TTACGGCACCTCGACCCCAAAAAACTTGATTTGGGTGATGGTTCACGTAGTGGGCCATCGCC
CTGATAGACGGTTTTTCGCCCTTTGACGTTGGAGTCCACGTTCTTTAATAGTGGACTCTTGT
TCCAAACTGGAACAACACTCAACCCTATCTCGGGCTATTCTTTTGATTTATAAGGGATTTTG
CCGATTTCGGCCTATTGGTTAAAAAATGAGCTGATTTAACAAAAATTTAACGCGAATTTTAA
CAAAATATTAACGTTTACAATTTTATGGTGCACTCTCAGTACAATCTGCTCTGATGCCGCAT
AGTTAAGCCAGCCCCGACACCCGCCAACACCCGCTGACGCGCCCTGACGGGCTTGTCTGCTC
CCGGCATCCGCTTACAGACAAGCTGTGACCGTCTCCGGGAGCTGCATGTGTCAGAGGTTTTC
ACCGTCATCACCGAAACGCGCGAGACGAAAGGGCCTCGTGATACGCCTATTTTATAGGTTA
ATGTCATGATAATAATGGTTTCTTAGACGTCAGGTGGCACTTTTCGGGGAAATGTGCGCGGA
ACCCCTATTTGTTTATTTTTCTAAATACATTCAAATATGTATCCGCTCATGAGACAATAACC
CTGATAAATGCTTCAATAATATTGAAAAGGAAGAGTATGAGTATTCAACATTTCCGTGTCG
CCCTTATTCCTTTTTTGCGGCATTTTGCCTTCCTGTTTTTGCTCACCCAGAAACGCTGGTGA
AAGTAAAAGATGCTGAAGATCAGTTGGGTGCACGAGTGGGTTACATCGAACTGGATCTCAAC
AGCGGTAAGATCCTTGAGAGTTTTCGCCCCGAAGAACGTTTTCCAATGATGAGCACTTTTAA
AGTTCTGCTATGTGGCGCGGTATTATCCCGTATTGACGCCGGGCAAGAGCAACTCGGTCGCC
GCATACACTATTCTCAGAATGACTTGGTTGAGTACTCACCAGTCACAGAAAAGCATCTTACG
GATGGCATGACAGTAAGAGAATTATGCAGTGCTGCCATAACCATGAGTGATAACACTGCGGC
CAACTTACTTCTGACAACGATCGGAGGACCGAAGGAGCTAACCGCTTTTTTGCACAACATGG
GGGATCATGTAACTCGCCTTGATCGTTGGGAACCGGAGCTGAATGAAGCCATACCAAACGAC
GAGCGTGACACCACGATGCCTGTAGCAATGGCAACAACGTTGCGCAAACTATTAACTGGCGA
ACTACTTACTCTAGCTTCCCGGCAACAATTAATAGACTGGATGGAGGCGGATAAAGTTGCAG
GACCACTTCTGCGCTCGGCCCTTCCGGCTGGCTGGTTTATTGCTGATAAATCTGGAGCCGGT
```

Figure 8 (Part 1)

```
GAGCGTGGGTCTCGCGGTATCATTGCAGCACTGGGGCCAGATGGTAAGCCCTCCCGTATCGT
AGTTATCTACACGACGGGGAGTCAGGCAACTATGGATGAACGAAATAGACAGATCGCTGAGA
TAGGTGCCTCACTGATTAAGCATTGGTAACTGTCAGACCAAGTTTACTCATATATACTTTAG
ATTGATTTAAAACTTCATTTTTAATTTAAAAGGATCTAGGTGAAGATCCTTTTTGATAATCT
CATGACCAAAATCCCTTAACGTGAGTTTTCGTTCCACTGAGCGTCAGACCCCGTAGAAAAGA
TCAAAGGATCTTCTTGAGATCCTTTTTTTCTGCGCGTAATCTGCTGCTTGCAAACAAAAAAA
CCACCGCTACCAGCGGTGGTTTGTTTGCCGGATCAAGAGCTACCAACTCTTTTTCCGAAGGT
AACTGGCTTCAGCAGAGCGCAGATACCAAATACTGTCCTTCTAGTGTAGCCGTAGTTAGGCC
ACCACTTCAAGAACTCTGTAGCACCGCCTACATACCTCGCTCTGCTAATCCTGTTACCAGTG
GCTGCTGCĊAGTGGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCTTGGAGCGAACGA
CCTACACCGAACTGAGATACCTACAGCGTGAGCTATGAGAAAGCGCCACGCTTCCCGAAGGG
AGAAAGGCGGACAGGTATCCGGTAAGCGGCAGGGTCGGAACAGGAGAGCGCACGAGGGAGCT
TCCAGGGGGAAACGCCTGGTATCTTTATAGTCCTGTCGGGTTTCGCCACCTCTGACTTGAGC
GTCGATTTTTGTGATGCTCGTCAGGGGGCGGAGCCTATGGAAAAACGCCAGCAACGCGGCC
TTTTTACGGTTCCTGGCCTTTTGCTGGCCTTTTGCTCACATGTTCTTTCCTGCGTTATCCCC
TGATTCTGTGGATAACCGTATTACCGCCTTTGAGTGAGCTGATACCGCTCGCCGCAGCCGAA
CGACCGAGCGCAGCGAGTCAGTGAGCGAGGAAGCGGAAGAGCGCCCAATACGCAAACCGCCT
CTCCCCGCGCGTTGGCCGATTCATTAATGCAGCTGGCACGACAGGTTTCCCGACTGGAAAGC
GGGCAGTGAGCGCAACGCAATTAATGTGAGTTAGCTCACTCATTAGGCACCCCAGGCTTTAC
ACTTTATGCTTCCGGCTCGTATGTTGTGTGGAATTGTGAGCGGATAACAATTTCACACAGGA
AACAGCTATGACCATGATTACGCC
```

Figure 8 (Part 2)

SEQUENCE LISTING

<160> NUMBER OF SEQ ID NOS: 13

<210> SEQ ID NO 1
<211> LENGTH: 37
<212> TYPE: DNA
<213> ORGANISM: Artificial Sequence
<220> FEATURE:
<223> OTHER INFORMATION: Primer

<400> SEQUENCE: 1
cagcttatca tcgataagct ttaatgcggt agtttat      37

<210> SEQ ID NO 2
<211> LENGTH: 38
<212> TYPE: DNA
<213> ORGANISM: Artificial Sequence
<220> FEATURE:
<223> OTHER INFORMATION: Primer

<400> SEQUENCE: 2
cgtagcccag cgcgtcggcc gccatgccgg cgataatg      38

<210> SEQ ID NO 3

```
<211> LENGTH: 59
<212> TYPE: DNA
<213> ORGANISM: Artificial Sequence
<220> FEATURE:
<223> OTHER INFORMATION: Primer

<400> SEQUENCE: 3
cactatggcg tgctgctagc gctatatgcg ttgatgcaat ttctatgagc acccgttct      59

<210> SEQ ID NO 4
<211> LENGTH: 65
<212> TYPE: DNA
<213> ORGANISM: Artificial Sequence
<220> FEATURE:
<223> OTHER INFORMATION: Primer

<400> SEQUENCE: 4
tctcaagggc atcggtcgac gctctcccct tatgcgactcc tgcattagga atcagcccag    60
tagta                                                                 65

<210> SEQ ID NO 5
<211> LENGTH: 710
<212> TYPE: DNA
<213> ORGANISM: Artificial Sequence
<220> FEATURE:
<223> OTHER INFORMATION: Theoretical insert

<400> SEQUENCE: 5
ctagcgctat atgcgttgat gcaatttcta tgagcacccg ttctcggagc actgtccgac      60
cgctttggcc gccgcccagt cctgctcgct tcgctacttg gagccactat cgactacgcg     120
atcatggcga ccacacccgt cctgtggatc ctctacgccg acgcatcgt ggccggcatc     180 accggcgcca caggtgcggt tgctggcgcc tatatcgccg acatcaccga tggggaagat    240
cgggctcgcc acttcgggct catgagcgct tgtttcggcg tgggtatggt ggcaggcccc    300
gtggccgggg gactgttggg cgccatctcc ttgcatgcac cattccttgc ggcggcggtg    360
ctcaacggcc tcaacctact actgggctgc ttcctaatgc aggagtcgca taagggagag    420
cgtcgaccga tgcccttgag agccttcaac ccagtcagct ccttccggtg ggcgcggggc    480
atgactatcg tcgccgcact tatgactgtc ttctttatca tgcaactcgt aggacaggtg    540
ccggcagcgc tctgggtcat tttcggcgag accgctttc gctggagcgc gacgatgatc     600
ggcctgtcgc ttgcggtatt cggaatcttg cacgccctcg ctcaagcctt cgtcactggt    660
cccgccacca aacgtttcgg cgagaagcag gccattatcg ccggcatggc                710

<210> SEQ ID NO 6
<211> LENGTH: 322
<212> TYPE: DNA
<213> ORGANISM: Artificial Sequence
<220> FEATURE:
<223> OTHER INFORMATION: Theoretical insert

<400> SEQUENCE: 6
gagccactat cgactacgcg atcatggcga ccacacccgt cctgtggatc ctctacgccg      60
gacgcatcgt ggccggcatc accggcgcca caggtgcggt tgctggcgcc tatatcgccg    120
acatcaccga tggggaagat cgggctcgcc acttcgggct catgagcgct tgtttcggcg    180
tgggtatggt ggcaggcccc gtggccgggg gactgttggg cgccatctcc ttgcatgcac    240
cattccttgc ggcggcggtg ctcaacggcc tcaacctact actgggctga ttcctaatgc    300
aggagtcgca taagggagag cg                                              322
```

<210> SEQ ID NO 7
<211> LENGTH: 645
<212> TYPE: DNA
<213> ORGANISM: Artificial Sequence
<220> FEATURE:
<223> OTHER INFORMATION: Experimentally determined sequence
<221> NAME/KEY: misc_feature
<222> LOCATION: (0)...(0)
<223> OTHER INFORMATION: N at any position may be A, T, G, or C

<400> SEQUENCE: 7

```
ccgttnaagn nnacacagtt anattgttaa ngcagtcagg caccgtgtat gaaatctaac      60
aatgcgctca tcgtcatcct cggnaccgtc accctggatg ttgtaggcat aggcttggtt     120
atgccggtac tgccgggcct cttgcgggat atcgtccatt ccgacagnat cgccagtcac     180
tatggngtgc tgctagcgct atatgcgttg atgcaatttc tatgagcacc cgttctcgga     240
gcactgtccg accgctttgg ccgccgccca gtcctgctcg cttcgctact tggagccact     300
atcgactacg cgatcatggc gaccacaccc gtcctgtgga tcctctacgc cggacgaatc     360
gatggccgga atcaccgggg tcacaggtgc ggntgctggn gcctatttcg ccgacatcaa     420
cgatggggaa agatcnggct cgncactncg ggctcatnag nntttggttt cggcntgggt     480
attggtngga agnccccan ggccgggggg attgttngng ngccaacttc cttggattga     540 acaatncct ngggggggg gggttcancn ggcncaacct attnntggga ttnttncnna     600
tnnagagtcg ataaggaggn gnnggccant ccntgnagcc caccc                     645
```

<210> SEQ ID NO 8
<211> LENGTH: 716
<212> TYPE: DNA
<213> ORGANISM: Artificial Sequence
<220> FEATURE:
<223> OTHER INFORMATION: Experimentally determined sequence
<221> NAME/KEY: misc_feature
<222> LOCATION: (0)...(0)
<223> OTHER INFORMATION: N at any position may be A, T, G, or C.

<400> SEQUENCE: 8

```
cagtatgacc atnnnctagc ttctcgncga gacgtttggt ngcnggacca gttacgaagg      60
cttgagcnag ggagttgaag attccntata ctnaatgnga taggnctatc atcggngggc     120
tccanagata gcggncancg ncnacanatg acccagagct ntgccggcan cagtcctacg     180
agtngnatga tnaagtagan aggcataatt ggggngacga tagtcatgnc ccgcggccac     240
cggaaggagc ttaatgggtt gnnggctctc aagggcatcg gtcgacgctc tcccttatgt     300
gactcntgna ttaggaatca gcccagttng ctaggtttgn ggccgnttgn aancaacccc     360
cgnccnnana gggaattgnt gnaatnnaaa gggngtttgg ngngcccaac aagtccccc     420 cgngcnanng ggggccctcc caccaattnc cccacggccg aaaaaaaang ttttcaatna     480
agccccnagg tngggaacc cctnttcttc ccccatcggn gganatttgg ntgaattttt     540
ggggnccaan anncccnnct ttngggtccg ntnttatntc ccncccacaa ttnnttcccg     600 tttngggnn nnntccnaan gaaggttttn tttccccccc natttccnct ttatncnntt     660
tntnntttnn nnatagaaaa anaaaantttt ggggngcca aggtttnata atattt         716
```

<210> SEQ ID NO 9
<211> LENGTH: 4054
<212> TYPE: DNA
<213> ORGANISM: Artificial Sequence
<220> FEATURE:

<223> OTHER INFORMATION: pEXmide V

<400> SEQUENCE: 9

```
aagcttgcat gcaaattcta tttcaaggag acagtcataa tgaaatacct attgcctacg      60
gcagccgctg gattgttatt actcgcggcc caaccggcca tggcatgagc ggccgcccgg     120
gcggcgcgcc ctgcaggcta gcactagtgg taccgtcgac aagaaagttg agcccaaatc     180
ttcaactaag acgcacacat caggaggtta gggtggcggt ggctctccat tcgtttgtga     240
atatcaaggc caatcgtctg acctgcctca acctcctgtc aatgctggcg gcggctctgg     300
tggtggttct ggtggcggct ctgagggtgg tggctctgag ggtggcggtt ctgagggtgg     360
cggctctgag ggaggcggtt ccggtggtgg ctctggttcc ggtgattttg attatgaaaa     420
gatggcaaac gctaataagg ggctatgacc gaaaatgcc gatgaaaacg cgctacagtc     480
tgacgctaaa ggcaaacttg attctgtcgc tactgattac ggtgctgcta tcgatggttt     540
cattggtgac gtttccggcc ttgctaatgg taatggtgct actggtgatt tgctggctc     600
taattcccaa atggctcaag tcggtgacgt tgataattca cctttaatga ataatttccg     660
tcaatattta ccttccctcc ctcaatcggt tgaatgtcgc ccttttgtct ttagcgctgg     720
taaaccatat gaattttcta ttgattgtga caaaataaac ttattccgtg gtgtctttgc     780
gttttctttta tatgttgcca cctttatgta tgtattttct acgtttgcta acatactgcg     840
taataaggag tcttaataag ggagcttgca tgcaaattct atttcaagga cacagtcata     900
atgaaatacc tattgcctac ggcagccgct ggattgttat tactgaattc actggccgtc     960
gttttacaac gtcgtgactg ggaaaaccct ggcgttaccc aacttaatcg ccttgcagca    1020
catccccctt tcgccagctg gcgtaatagc gaagaggccc gcaccgatcg cccttcccaa    1080
cagttgcgca gcctgaatgg cgaatggcgc tgatgcggt attttctcct tacgcatctg    1140
tgcggtattt cacaccgcat acgtcaaagc aaccatagta cgcgccctgt agcggcgcat    1200
taagcgcggc gggtgtggtg gttacgcgca gcgtgaccgc tacacttgcc agcgccctag    1260
cgcccgctcc tttcgctttc ttcccttcct ttctcgccac gttcgccggc tttccccgtc    1320
aagctctaaa tcggggctc cctttagggt tccgatttag tgctttacgg cacctcgacc    1380
ccaaaaaact tgatttgggt gatggttcac gtagtgggcc atcgccctga tagacggttt    1440
ttcgcccttt gacgttggag tccacgttct ttaatagtgg actcttgttc caaactggaa    1500
caacactcaa ccctatctcg ggctattctt ttgatttata agggattttg ccgatttcgg    1560
cctattggtt aaaaaatgag ctgatttaac aaaaatttaa cgcgaatttt aacaaaatat    1620
taacgtttac aattttatgg tgcactctca gtacaatctg ctctgatgcc gcatagttaa    1680
gccagccccg acacccgcca cacccgctg acgcgccctg acgggcttgt ctgctcccgg    1740
catccgctta cagacaagct gtgaccgtct ccggagctg catgtgtcag aggttttcac    1800
cgtcatcacc gaaacgcgcg agacgaaagg cctcgtgat acgcctattt ttataggtta    1860
atgtcatgat aataatggtt tcttagacgt caggtggcac ttttcgggga atgtgcgcg    1920
gaaccctat ttgtttattt ttctaaatac attcaaatat gtatccgctc atgagacaat    1980
aaccctgata aatgcttcaa taatattgaa aaaggaagag tatgagtatt caacatttcc    2040
gtgtcgccct tattcctttt ttgcggcatt ttgccttcct gtttttgctc acccagaaac    2100
gctggtgaaa gtaaaagatg ctgaagatca gttgggtgca cgagtgggtt acatcgaact    2160
ggatctcaac agcggtaaga tccttgagag ttttcgcccc gaagaacgtt ttccaatgat    2220
gagcactttt aaagttctgc tatgtggcgc ggtattatcc cgtattgacg ccgggcaaga    2280
```

```
gcaactcggt cgccgcatac actattctca gaatgacttg gttgagtact caccagtcac    2340
agaaaagcat cttacggatg gcatgacagt aagagaatta tgcagtgctg ccataaccat    2400
gagtgataac actgcggcca acttactcct gacaacgatc ggaggaccga aggagctaac    2460
cgcttttttg cacaacatgg gggatcatgt aactcgcctt gatcgttggg aaccggagct    2520
gaatgaagcc ataccaaacg acgagcgtga caccacgatg cctgtagcaa tggcaacaac    2580
gttgcgcaaa ctattaactg gcgaactact tactctagct tcccggcaac aattaataga    2640
ctggatggag gcggataaag ttgcaggacc acttctgcgc tcggcccttc cggctggctg    2700
gtttattgct gataaatctg gagccggtga gcgtgggtct cgcggtatca ttgcagcact    2760
ggggccagat ggtaagccct cccgtatcgt agttatctac acgacgggga gtcaggcaac    2820
tatggatgaa cgaaatagac agatcgctga gataggtgcc tcactgatta agcattggta    2880
actgtcagac caagtttact catatatact ttagattgat ttaaaacttc atttttaatt    2940
taaaaggatc taggtgaaga tcctttttga taatctcatg accaaaatcc cttaacgtga    3000
gttttcgttc cactgagcgt cagacccgt agaaaagatc aaaggatctt cttgagatcc    3060
tttttttctg cgcgtaatct gctgcttgca acaaaaaaa ccaccgctac cagcggtggt    3120
ttgtttgccg gatcaagagc taccaactct ttttccgaag gtaactggct tcagcagagc    3180
gcagatacca aatactgtcc ttctagtgta gccgtagtta ggccaccact tcaagaactc    3240
tgtagcaccg cctacatacc tcgctctgct aatcctgtta ccagtggctg ctgccagtgg    3300
cgataagtcg tgtcttaccg ggttggactc aagacgatag ttaccggata aggcgcagcg    3360
gtcgggctga acggggggtt cgtgcacaca gcccagcttg gagcgaacga cctacaccga    3420
actgagatac ctacagcgtg agctatgaga aagcgccacg cttcccgaag ggagaaaggc    3480
ggacaggtat ccggtaagcg gcagggtcgg aacaggagag cgcacgaggg agcttccagg    3540
gggaaacgcc tggtatcttt atagtcctgt cgggtttcgc cacctctgac ttgagcgtcg    3600
atttttgtga tgctcgtcag ggggcggag cctatggaaa aacgccagca acgcggcctt    3660
tttacggttc ctggcctttt gctggccttt tgctcacatg ttctttcctg cgttatcccc    3720
tgattctgtg gataaccgta ttaccgcctt tgagtgagct gataccgctc gccgcagccg    3780
aacgaccgag cgcagcgagt cagtgagcga ggaagcggaa gagcgcccaa tacgcaaacc    3840
gcctctcccc gcgcgttggc cgattcatta atgcagctgg cacgacaggt ttcccgactg    3900
gaaagcgggc agtgagcgca acgcaattaa tgtgagttag ctcactcatt aggcacccca    3960
ggctttacac tttatgcttc cggctcgtat gttgtgtgga attgtgagcg gataacaatt    4020
tcacacagga aacagctatg accatgatta cgcc                                4054

<210> SEQ ID NO 10
<211> LENGTH: 61
<212> TYPE: DNA
<213> ORGANISM: Artificial Sequence
<220> FEATURE:
<223> OTHER INFORMATION: Primer

<400> SEQUENCE: 10
caactttctt gtcgacttta tcatcatcat ctttataatc acctaggacc gtcagcttgg    60
t                                                                     61

<210> SEQ ID NO 11
<211> LENGTH: 43
<212> TYPE: DNA
```

-continued

```
<213> ORGANISM: Artificial Sequence
<220> FEATURE:
<223> OTHER INFORMATION: Primer

<400> SEQUENCE: 11
actcgcggcc caaccggcca tggccgaggt gcagctgttg gag                        43

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
ggagagccac cgccacccta ac                                              22

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
tcacacagga aacagctatg ac                                              22
```

METHOD FOR IN VITRO MOLECULAR EVOLUTION OF PROTEIN FUNCTION

This application claims priority under 35 U.S.C. §119(e) to PCT/GB98/01757 entitled "A method for in vitro evolution of protein function" filed Jun. 16, 1998, which in turn claims priority from GB application 9712512.4 filed Jun. 16, 1997, the entire disclosure of each being incorporated by reference herein.

FIELD OF THE INVENTION

The present invention relates to a method for in vitro molecular evolution of protein function, in particular by shuffling of DNA segments obtained using an exonuclease.

BACKGROUND OF THE INVENTION

Protein function can be modified and improved in vitro by a variety of methods, including site directed mutagenesis (Alber et al, Nature, 5; 330(6143):41–46, 1987) combinatorial cloning (Huse et al, Science, 246:1275–1281, 1989; Marks et al, Biotechnology, 10: 779–783, 1992) and random mutagenesis combined with appropriate selection systems (Barbas et al, PNAS. USA, 89: 4457–4461, 1992).

The method of random mutagenesis together with selection has been used in a number of cases to improve protein function and two different strategies exist. Firstly, randomisation of the entire gene sequence in combination with the selection of a variant (mutant) protein with the desired characteristics, followed by a new round of random mutagenesis and selection. This method can then be repeated until a protein variant is found which is considered optimal (Schier R. et al, J. Mol. Biol. 1996 263 (4): 551–567). Here, the traditional route to introduce mutations is by error prone PCR (Leung et al, Technique, 1: 11–15, 1989) with a mutation rate of ≈0.7%. Secondly, defined regions of the gene can be mutagenized with degenerate primers, which allows for mutation rates up to 100% (Griffiths et al, EMBO. J, 13: 3245–3260, 1994; Yang et al, J. Mol. Biol. 254: 392–403, 1995). The higher the mutation rate used, the more limited the region of the gene that can be subjected to mutations.

Random mutation has been used extensively in the field of antibody engineering. In vivo formed antibody genes can be cloned in vitro (Larrick et al, Biochem. Biophys. Res. Commun. 160: 1250–1256, 1989) and random combinations of the genes encoding the variable heavy and light genes can be subjected to selection (Marks et al, Biotechnology, 10: 779–783, 1992). Functional antibody fragments selected can be further improved using random mutagenesis and additional rounds of selections (Schier R. et al, J. Mol. Biol. 1996 263 (4): 551–567) .

The strategy of random mutagenesis is followed by selection. Variants with interesting characteristics can be selected and the mutated DNA regions from different variants, each with interesting characteristics, are combined into one coding sequence (Yang et al, J. Mol. Biol. 254: 392–403, 1995). This is a multi-step sequential process, and potential synergistic effects of different mutations in different regions can be lost, since they are not subjected to selection in combination. Thus, these two strategies do not include simultaneous mutagenesis of defined regions and selection of a combination of these regions. Another process involves combinatorial pairing of genes which can be used to improve eg antibody affinity (Marks et al, Biotechnology, 10: 779–783, 1992). Here, the three CDR-regions in each variable gene are fixed and this technology does not allow for shuffling of individual gene segments in the gene for the variable domain, for example, including the CDR regions, between clones.

The concept of DNA shuffling (Stemmer, Nature 370: 389–391, 1994) utilizes random fragmentation of DNA and assembly of fragments into a functional coding sequence. In this process it is possible to introduce chemically synthesized DNA sequences and in this way target variation to defined places in the gene which DNA sequence is known (Crameri et al, Biotechniques, 18: 194–196, 1995). In theory, it is also possible to shuffle DNA between any clones. However, if the resulting shuffled gene is to be functional with respect to expression and activity, the clones to be shuffled have to be related or even identical with the exception of a low level of random mutations. DNA shuffling between genetically different clones will generally produce non-functional genes.

Selection of functional proteins from molecular libraries has been revolutionized by the development of the phage display technology (Parmley et al, Gene, 73: 305–391 1988; McCafferty et al, Nature, 348: 552–554, 1990; Barbas et al, PNAS. USA, 88: 7978–7982, 1991). Here, the phenotype (protein) is directly linked to its corresponding genotype (DNA) and this allows for directly cloning of the genetic material which can then be subjected to further modifications in order to improve protein function. Phage display has been used to clone functional binders from a variety of molecular libraries with up to $10^{11}$ transformants in size (Griffiths et al, EMBO. J. 13: 3245–3260, 1994). Thus, phage display can be used to directly clone functional binders from molecular libraries, and can also be used to improve further the clones originally selected.

Random combination of DNA from different mutated clones in combination with selection of desired function is a more efficient way to search through sequence space as compared to sequential selection and combination of selected clones.

SUMMARY OF THE INVENTION

According to one aspect of the present invention, there is provided a method for generating a polynucleotide sequence or population of sequences from a parent polynucleotide sequence encoding one or more protein motifs, comprising the steps of a) digesting the parent polynucleotide sequence with an exonuclease to generate a population of fragments;

b) contacting said fragments with a template polynucleotide sequence under annealing conditions;

c) amplifying the fragments that anneal to the template in step b) to generate at least one polynucleotide sequence encoding one or more protein motifs having altered characteristics as compared to the one or more protein motifs encoded by said parent polynucleotide.

The parent polynucleotide is preferably double-stranded and the method further comprises the step of generating single-stranded polynucleotide sequence from said double-stranded fragments prior to step b). Further, the template polynucleotide is preferably the parent polynucleotide sequence or at least a polynucleotide sequence having sequence in common with the parent nucleotide sequence so that the fragments will hybridize with the template under annealing conditions. For example, if the parent polynucleotide is an antibody, the template may be a different antibody having constant domains or framework regions in common.

Therefore, typically, there is provided a method of combining polynucleotide fragments to generate a polynucleotide sequence or population of sequences of desired characteristics, which method comprises the steps of:
(a) digesting a linear parent double-stranded polynucleotide encoding one or more protein motifs with an exonuclease to generate a population of double stranded fragments of varying lengths;
(b) obtaining single-stranded polynucleotides from said double-stranded fragments; and
(c) assembling a polynucleotide sequence from the sequences derived from step (b).

Preferably the method further comprises the step of (d) expressing the resulting protein encoded by the assembled polynucleotide sequence and screening the protein for desired characteristics.

Prior to assembling the polynucleotide sequence in step (c) the double stranded sequences are preferably purified and then mixed in order to facilitate assembly. By controlling the reaction time of the exonuclease the size of the polynucleotide fragments may be determined. Determining the lengths of the polynucleotide fragments in this way avoids the necessity of having to provide a further step such as purifying the fragments of desired length from a gel.

Further, as some exonuclease digests polynucleotide sequences from both the 3' and the 5' ends, the fragments selected may center around the middle of the gene sequence if this particular region of sequence is desired. This sequence from the middle of a gene may be mutated randomly by, for example, error prone PCR and desirable for the shuffling process.

However, in some cases it may be desirable not to shuffle the sequence from the middle of the gene. This may be prevented by choosing long fragments after exonuclease treatment. Conversely, if it is desirable to shuffle the middle of the gene sequence short exonuclease treated fragments may be used.

In order to generate a polynucleotide sequence of desired characteristics the parent double-stranded polynucleotide encoding one or more protein motifs may be subjected to mutagenesis to create a plurality of differently mutated derivatives thereof. Likewise, a parent double-stranded polynucleotide may be obtained already encoding a plurality of variant protein motifs of unknown sequence.

Random mutation can be accomplished by any conventional method as described above, but a suitable method is error-prone PCR.

It is preferable to use PCR technology to assemble the single-stranded polynucleotide fragments into the double-stranded polynucleotide sequence.

The polynucleotide sequence is preferably DNA although RNA may be used. For simplicity the term polynucleotide will now be used in the following text in relation to DNA but it will be appreciated that the present invention is applicable to both RNA and DNA.

Any exonuclease that digests polynucleotide from the 3' prime end to the 5' prime end or from both the 3' and the 5' end may be used. Examples of a suitable exonuclease which may be used in accordance with the present invention include BAL31 and Exonuclease III.

BAL31 is a exonuclease that digests and removes nucleotide bases from both the 3' and the 5' ends of a linear polynucleotide molecule. The enzyme uses Ca2+ as a co-factor which can be bound in complex with EGTA (Ethylene Glycol bis(β-amino ethyl Ether) N,N,N',N'-tetra acetic acid). EGTA does not bind Mg2+ which is necessary for the subsequent PCR process. Linear DNA sequences are digested with BAL31 and the reaction stopped at different time points by the addition of EGTA. The individual digested fragments are purified, mixed and reassembled with PCR technology. The assembled (reconstituted) gene may then be cloned into an expression vector for expressing the protein. The protein may then be analyzed for improved characteristics.

The PCR technique uses a template, which may be the wild type sequence or a reconstituted sequence in accordance with the present invention. The fragments hybridize with the template at the appropriate regions (i.e. where the homology between the two strands is at its highest) and the remaining sequence is generated by elongation of the fragment using the template in accordance with the PCR technique.

The method of the present invention provides several advantages over known shuffling techniques. For example, in other DNA shuffling techniques the process itself introduces mutations over the entire gene sequence. The present invention allows for the concentration of mutations on i) the flanking regions after recombination of wild type fragments on either an already recombined template created by the method of the present invention, a template mutated in any other way or a gene (or gene combination, for example, a combination of antibody genes) having a desired sequence; or ii) the middle region after recombination of mutated fragments created by the method of the present invention on a wild type template.

In other words, if it is desirable to provide a gene having mutations concentrated in its flanking regions, a wild type fragment relating to the middle region of the gene may be used in conjunction with a reconstituted and/or mutated template sequence for the PCR process. In this way, the PCR process generates complementary sequence to the reconstituted/mutated template sequence as it elongates the wild type fragment. Therefore, the resulting sequence will have substantially a middle region corresponding to the wild type sequence and flanking regions with incorporated mutations.

Conversely, if it is desirable to provide a gene having mutations concentrated in its middle region, a reconstituted and or mutated fragment corresponding to the middle region of the gene may be used in conjunction with a wild type template in the PCR process. In this way, the PCR process, by elongating the mutated fragment using the wild type template, generates a sequence having substantially a mutated middle region and wild type flanking regions.

Further, the method of the present invention produces a set of progressively shortened DNA fragments for each time point a DNA sample is taken from the BAL31 treatment. The DNA samples may be collected and pooled together or, optionally, individual samples may be chosen and used in the method. Thus the present invention allows a selection of what DNA samples are to be used in the recombination system and thereby offers a further degree of control.

The method of the present invention may be carried out on any polynucleotide which codes for a particular product for example any protein having binding or catalytical properties e.g. antibodies or parts of antibodies, enzymes or receptors. Further, any polynucleotide that has a function that may be altered for example catalytical RNA may be shuffled in accordance with the present invention. It is preferable that the parent polynucleotide encoding one or more protein motif is at least 12 nucleotides in length, more preferably at least 20 nucleotides in length, even more preferably more than 50 nucleotides in length. Polynucleotides being at least 100 nucleotides in length or even at least 200 nucleotides in length may be used. Where parent polynucleotides are used that encoded for large proteins such as enzymes or antibodies, these may be many hundreds or thousands of bases in length. The present invention may be carried out on any size of parent polynucleotide.

The present invention also provides polynucleotide sequences generated by the method described above having desired characteristics. These sequences may be used for generating gene therapy vectors and replication-defective gene therapy constructs or vaccination vectors for DNA-based vaccinations. Further, the polynucleotide sequences may be used as research tools.

The present invention also provides a polynucleotide library of sequences generated by the method described above from which a polynucleotide may be selected which encodes a protein having the desired characteristics. It is preferable that the polynucleotide library is a DNA or cDNA library.

The present inventions also provides proteins such as antibodies, enzymes, and receptors having characteristics different to that of the wild type produced by the method described above. These proteins may be used individually or within a pharmaceutically acceptable carrier as vaccines or medicaments for therapy, for example, as immunogens, antigens or otherwise in obtaining specific antibodies. They may also be used as research tools.

The desired characteristics of a polynucleotide generated by the present invention or a protein encoded by a polynucleotide generated by the present invention may be any variation in the normal activity of the wild type (parent) polynucleotide or the polypeptide, protein or protein motifs it encodes. For example, it may be desirable to reduce or increase the catalytic activity of an enzyme, or improve or reduce the binding specificity of an antibody. Further, if the protein, or polynucleotide is an immunogen, it may be desirable to reduce or increase its ability to obtain specific antibodies against it. The parent polynucleotide preferably encodes one or more protein motifs. These are defined by regions of polynucleotide sequence that encode polypeptide sequence having or potentially having characteristic protein function. For example, a protein motif may define a portion of a whole protein, i.e. an epitope or a cleavage site or a catalytic site etc. However, within the scope of the present invention, an expressed protein motif does not have to display activity, or be "correctly" folded.

It may be desirable to modify a protein so as to alter the conformation of certain epitopes, thereby improving its antigenicity and/or reducing cross-reactivity. For example, should such a protein be used as an antigen, the modification may reduce any cross-reaction of raised antibodies with similar proteins.

Although the term "enzyme" is used, this is to interpreted as also including any polypeptide having enzyme-like activity, i.e. a catalytic function. For example, polypeptides being part of an enzyme may still possess catalytic function. Likewise, the term "antibody" should be construed as covering any binding substance having a binding domain with the required specificity. This includes antibody fragments, derivatives, functional equivalents and homologues of antibodies, including synthetic molecules and molecules whose shape mimics that of an antibody enabling it to bind an antigen or epitope. Examples of antibody fragments, capable of binding an antigen or other binding partner are Fab fragment consisting of the VL, VH, Cl and CH1 domains, the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

In order to obtain expression of the generated polynucleotide sequence, the sequence may be incorporated in a vector having control sequences operably linked to the polynucleotide sequence to control its expression. The vectors may include other sequences such as promoters or enhancers to drive the expression of the inserted polynucleotide sequence, further polynucleotide sequences so that the protein encoded for by the polynucleotide is produced as a fusion and/or nucleic acid encoding secretion signals so that the protein produced in the host cell is secreted from the cell. The protein encoded for by the polynucleotide sequence can then be obtained by transforming the vectors into host cells in which the vector is functional, culturing the host cells so that the protein is produced and recovering the protein from the host cells or the surrounding medium. Prokaryotic and eukaryotic cells are used for this purpose in the art, including strains of *E. coli*, yeast, and eukaryotic cells such as COS or CHO cells. The choice of host cell can be used to control the properties of the protein expressed in those cells, e.g. controlling where the protein is deposited in the host cells or affecting properties such as its glycosylation.

The protein encoded by the polynucleotide sequence may be expressed by methods well known in the art. Conveniently, expression may be achieved by growing a host cell in culture, containing such a vector, under appropriate conditions which cause or allow expression of the protein.

Systems for cloning and expression of a protein in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of polynucleotide sequences, for example in preparation of polynucleotide constructs, mutagenesis, sequencing, introduction of DNA into cells and gene expression, and analysis of proteins, are described in detail in Current Protocols in Molecular Biology, Ausubel et al. eds., John Wiley & Sons, 1992.

The FIND system can be used for the creation of DNA libraries comprising variable sequences which can be screened for the desired protein function in a number of ways. Phage display may be used for selecting binding (Griffith et al., EMBO J. 113: 3245–3260, 1994); screening for enzyme function (Crameri A. et al, Nature 1998 15; 391 (6664):288–291; Zhang J. H. et al, PNAS. USA 1997 94 (9): 4504–4509; Warren M. S. et al, Biochemistry 1996, 9; 35(27): 8855–8862).

A protein provided by the present invention may be used in screening for molecules which affect or modulate its activity or function. Such molecules may be useful in a therapeutic (possibly including prophylactic) context.

The present invention also provides vectors comprising polynucleotide sequences generated by the method described above.

The present inventions also provides compositions comprising either polynucleotide sequences, vectors comprising the polynucleotide sequences or proteins generated by the method described above and a pharmaceutically acceptable carrier or a carrier suitable for research purposes.

The present invention also provides a method comprising, following the identification of the polynucleotide or polypeptide having desired characteristics by the method described above, the manufacture of that polypeptide or polynucleotide in whole or in part, optionally in conjunction with additional polypeptides or polynucleotides.

Following the identification of a polynucleotide or polypeptide having desired characteristics, these can then be manufactured to provide greater numbers by well known techniques such as PCR, cloning a expression within a host cell. The resulting polypeptides or polynucleotides may be used in the preparation of medicaments for diagnostic use, pharmaceutical use, therapy etc. This is discussed further below. Alternatively, the manufactured polynucleotide, polypeptide may be used as a research tool, i.e. antibodies may be used in immunoassays, polynucleotides may be used a hybridization probes or primers.

The polypeptides or polynucleotides generated by the method of the invention and identified as having desirable characteristics can be formulated in pharmaceutical compositions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

Whether it is a polypeptide, e.g. an antibody or fragment thereof, an enzyme, a polynucleotide or nucleic acid molecule, identified following generation by the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, e.g. in a viral vector (a variant of the VDEPT technique). The vector could be targeted to the specific cells to be treated, or it could contain regulatory elements which are switched on more or less selectively by the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. an enzyme, in a vector by expression from encoding DNA in a viral vector (see for example, EP-A-415731 and WO 90/07936).

A composition may be administered alone or in combination with other treatments, either simultaneously or sequentially dependent upon the condition to be treated.

As a further alternative, the polynucleotide identified as having desirable characteristics following generation by the method of the present invention could be used in a method of gene therapy, to treat a patient who is unable to synthesize the active polypeptide encoded by the polynucleotide or unable to synthesize it at the normal level, thereby providing the effect provided by the corresponding wild-type protein.

Vectors such as viral vectors have been used in the prior art to introduce polynucleotides into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted tumour cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpes viruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

As mentioned above, the aim of gene therapy using nucleic acid encoding a polypeptide, or an active portion thereof, is to increase the amount of the expression product of the nucleic acid in cells in which the level of the wild-type polypeptide is absent or present only at reduced levels. Such treatment may be therapeutic in the treatment of cells which are already cancerous or prophylactic in the treatment of individuals known through screening to have a susceptibility allele and hence a predisposition to, for example, cancer.

The present invention also provides a kit for generating a polynucleotide sequence or population of sequences of desired characteristics comprising an exonuclease and components for carrying out a PCR technique, for example, thermostable DNA (nucleotides) and a stopping device, for example, EGTA.

The present applicants have termed the technology described above as FIND (Fragment Induced Nucleotide Diversity).

As outlined above, the FIND programme, in accordance with the present invention conveniently provides for the creation of mutated antibody gene sequences and their random combination to functional antibodies having desirable characteristics. As an example of this aspect of the invention, the antibody genes are mutated by error prone PCR which results in a mutation rate of approximately 0.7%. The resulting pool of mutated antibody genes are then digested with an exonuclease, preferably BAL31, and the reaction inhibited by the addition of EGTA at different time points, resulting in a set of DNA fragments of different sizes. These may then be subjected to PCR based reassembly as described above. The resulting reassembled DNA fragments are then cloned and a gene library constructed. Clones may then be selected from this library and sequenced.

A further application of the FIND technology is the generation of a population of variable DNA sequences which can be used for further selections and analyses. Besides encoding larger proteins, e.g. antibody fragments and enzymes, the DNA may encode peptides where the molecules functional characteristics can be used for the design of different selection systems. Selection of recombined DNA sequences encoding peptides has previously been described (Fisch et al PNAS. USA Jul. 23, 1996; 93 (15): 7761–7766). In addition, the variable DNA population can be used to produce a population of RNA molecules with e.g. catalytic activities. Vaish et al (PNAS. USA Mar. 3, 1998; 95 (5): 2158–2162) demonstrated the design of functional systems for the selection of catalytic RNA and Eckstein F (Ciba Found. Symp. 1997; 209; 207–212) has outlined the applications of catalytic RNA by the specific introduction of catalytic RNA in cells. The FIND system may be used to further search through the sequence space in the selection of functional peptides/molecules with catalytic activities based on recombined DNA sequences.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

FIG. 6 shows A) the theoretical insert after restriction digestion of the fragment resulting from the primer combination FIND 1, pBR322 NheI-forward —STOP—primer with pBR322-EagI-reversed-primer. This is termed FIND 1 and SEQ ID #5; and B) the theoretical insert after restriction digestion of the fragment resulting from the primer combination pBR322 HindIII forward primer and pBR322 SalI reverse stop primer. This is termed FIND 3 and SEQ ID #6; and FIG. 7 shows the experimentally determined sequences of the 2 first FIND clones after automated sequencing. A) shows FIND 1 sequence with the STOP codon marked in bold (SEQ ID #7); and B) shows the FIND 3 sequence with the STOP codon shown in underline text (SEQ ID #8).

FIG. 8 shows the sequence of pEXmide V (4055 bp) NcoI- and Sal I-sites are marked in underlined text (SEQ ID #9).

DETAILED DESCRIPTION AND EXEMPLIFICATION OF THE INVENTION

Figure 1:
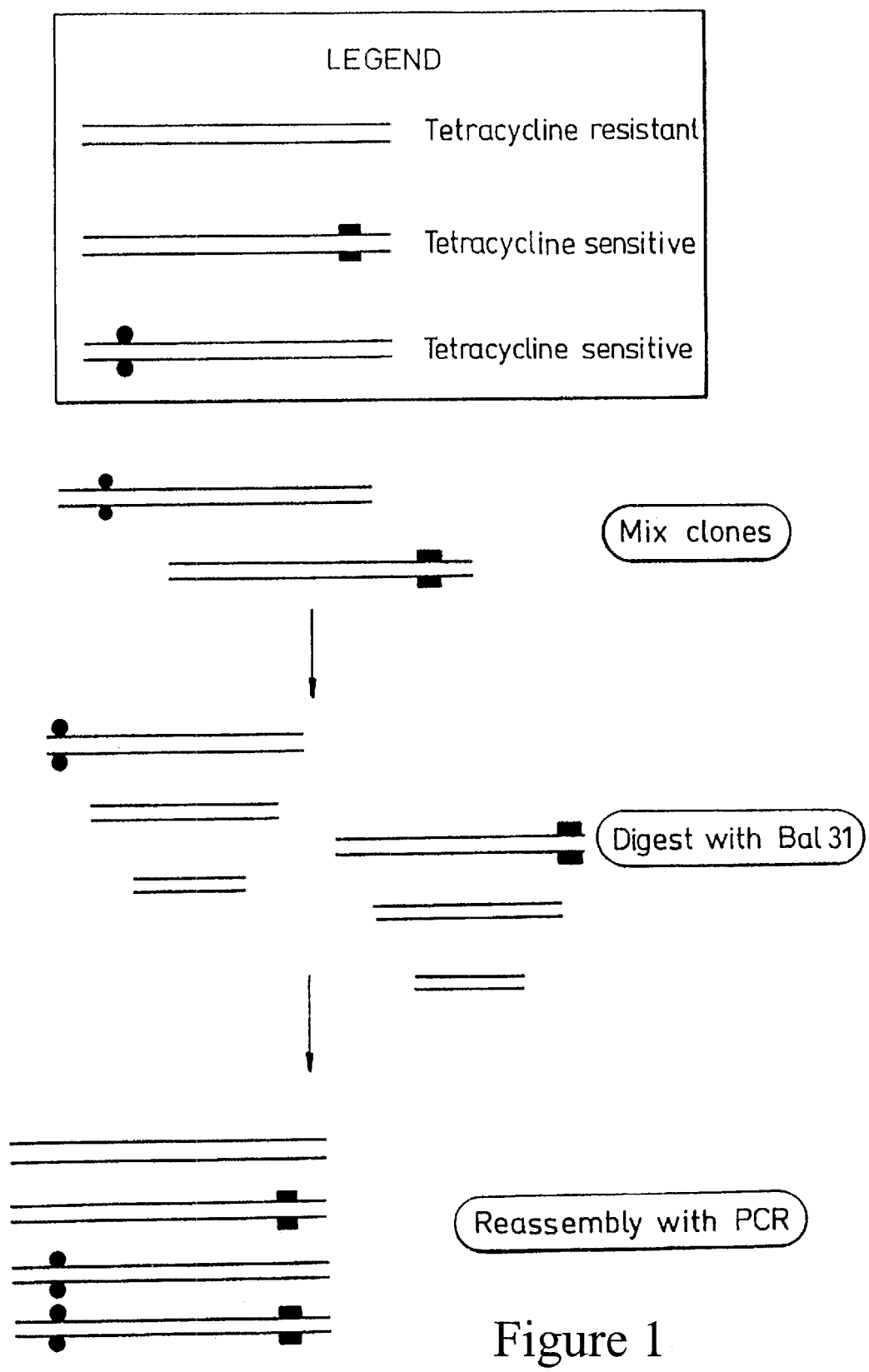
FIG. 1 shows the principle steps in the shuffling of specific DNA sequences between different clones.
Figure 2:
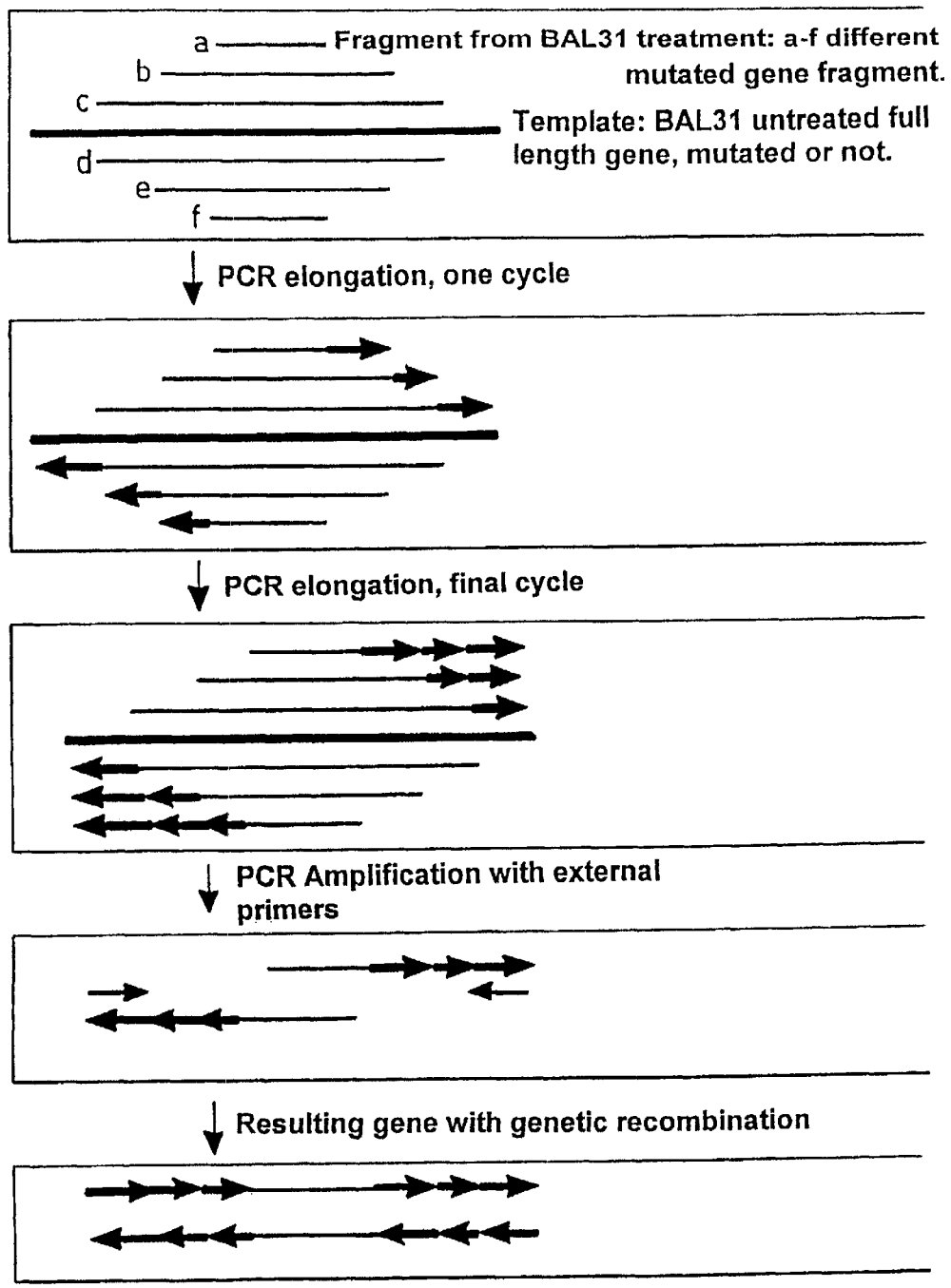
FIG. 2 shows the principle steps in the PCR elongation of exonuclease treated gene sequences.
Figure 3:
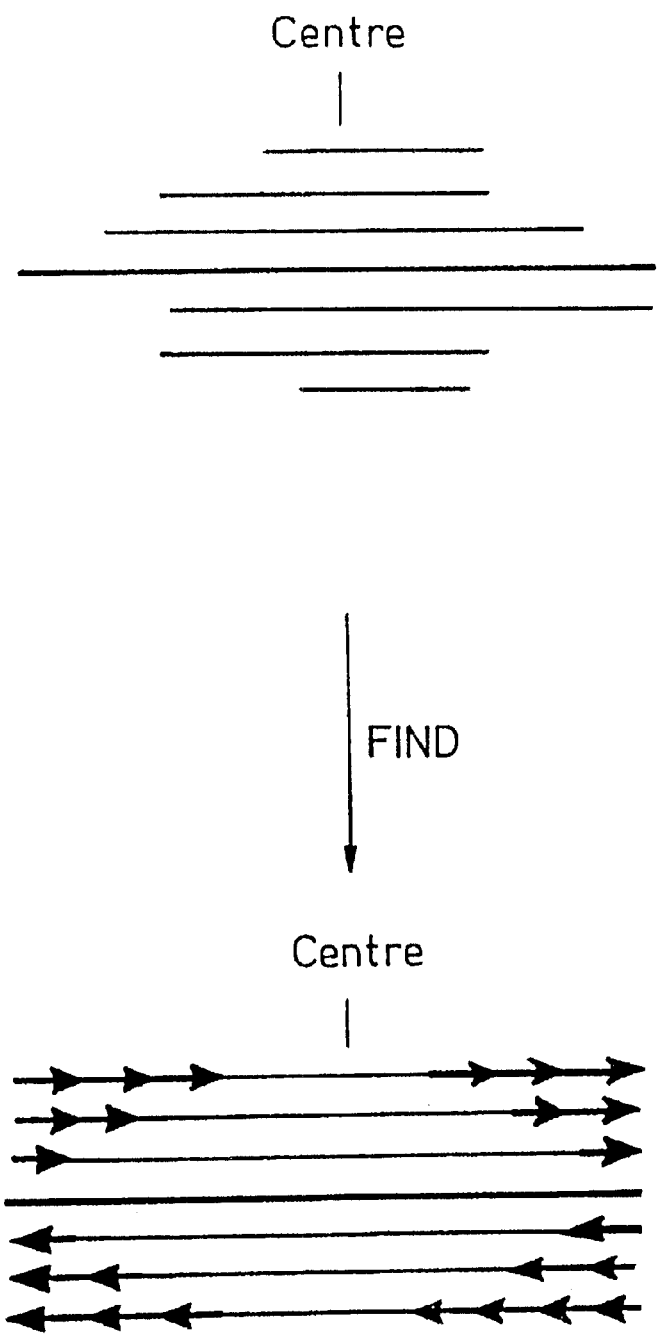
FIG. 3 shows the principle steps in the PCR elongation of long fragments of exonuclease treated gene sequences. The use of long fragments results in the middle region of the gene not being recombined. This region may however contain random mutations and the middle of the gene sequence may thus differ form other clones. The middle region of the sequence may differ in length, but by using longer primers the middle region may be covered.
Figure 4:
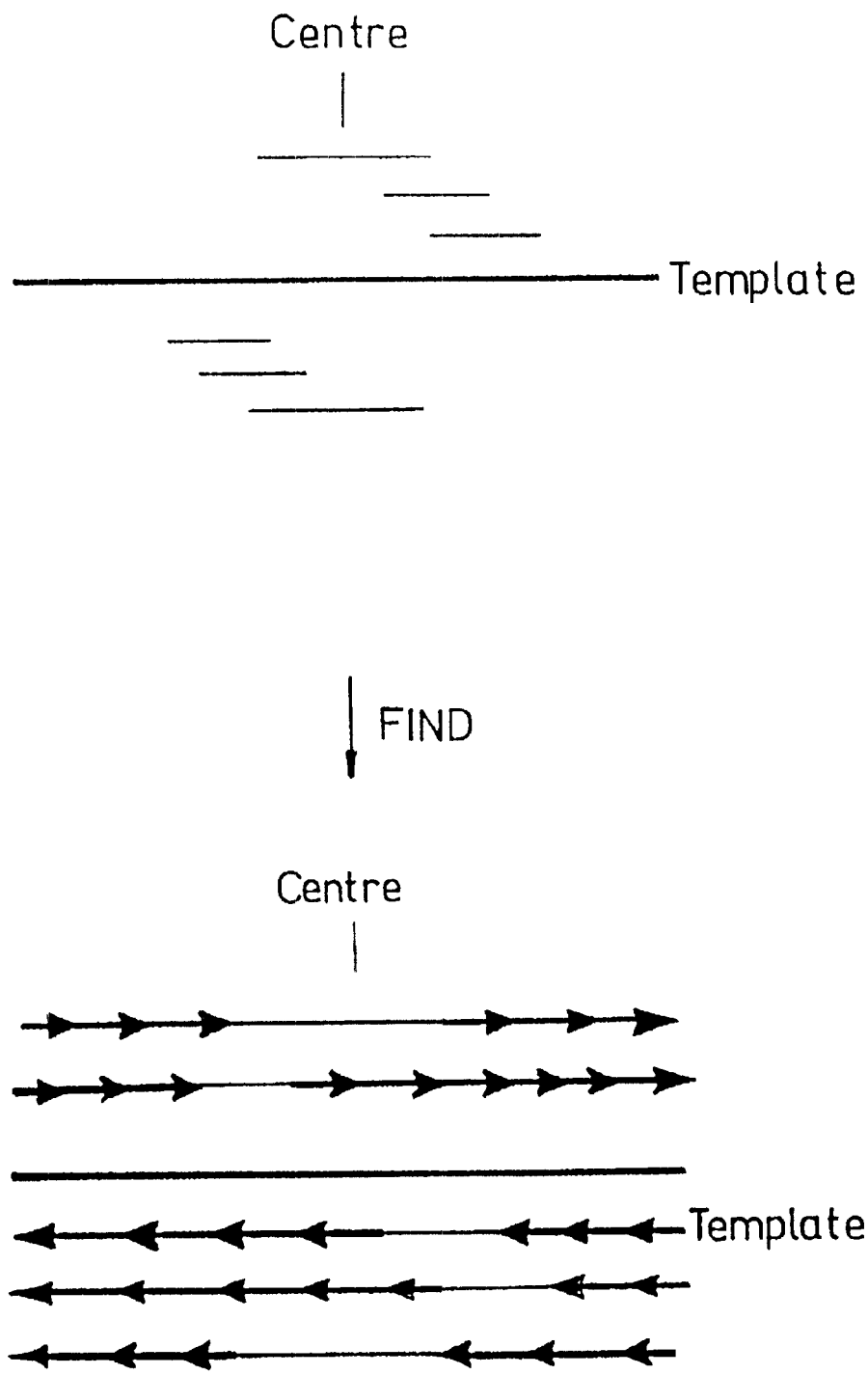
FIG. 4 shows the principle steps in the PCR elongation of short fragments of exonuclease treated gene sequences. The use of short fragments results in the middle region of the gene being recombined. If a longer reaction time is used for the exonuclease digestion a set of fragments of differing lengths are produced. If the fragments are short, some fragments will be located away from the middle region of the gene sequence thereby allowing recombination of the middle sequence.

One aspect of the DNA shuffling procedure can be illustrated by the steps shown in FIG. 1. The gene encoding the tetracycline-resistance (Tet-R) in the plasmid. pBR322 is used in this example. Two clones were generated by site directed mutagenesis: one with an engineered stop codon close to the 5' terminus and one with a stop codon close to the 3' terminus of the Tet-R gene. The phenotype of these two genes is tetracycline sensitive. By mixing the two clones in equimolar amounts and digesting with BAL31 revertants were selected. After cloning the reassembled genes (with combination between the two genes carrying the two stop codons) revertants with a frequency of 16% were detected, i.e. 16% of the clones were tetracycline resistant. The experiment used the ampicillin-resistance in pBR322 for primary selection and then individual Amp-R clones were tested under tetracycline selection (see the overview in FIG. 1 and the theoretical view in FIG. 2).

A more detailed description of examples of the present invention are given below.

Reagents

AmpliTaq® polymerase was purchased from Perkin-Elmer Corp., dNTPs from Boehringer Mannheim Biochemica (Mannheim, Germany), and BAL31 Nuclease from New England Biolabs Inc. (Beverly, USA). Klenow enzyme was purchased from Amersham. All restriction enzymes were purchased from Boehringer Mannheim Biochemica (Mannheim, Germany). Ethidium bromide was purchased from Bio-Rad Laboratories (Bio-Rad Laboratories, Hercules, Calif., USA). T4 DNA Ligase was purchased from Appligene Inc. (Pleasanton, Calif., USA).

All primers were designed in the laboratory and synthesized with an Applied Biosystems 391 DNA-synthesiser.

PCR

All Polymerase Chain Reactions (PCR) were carried out in a automatic thermocycler (Perkin-Elmer Cetus 480, Norwalk, Conn., USA). PCR techniques for the amplification of nucleic acid are described in U.S. Pat. No. 4,683,195. The PCR reactions were run at varying amounts of cycles consisting of following profile: denaturation (94° C., 1 minute), primer annealing (55° C., 1 minute) and extension (72° C., 1 minute) using a 1 second ramp time. The PCR reactions contained, unless otherwise noted, 5 µl of each primer (20 µM), 8 µl of dNTP (1.25 mM each of dTTP, DATP, dCTP and dGTP), 10 µl 10×reaction buffer, 0.5 µl AmpliTaq® thermostable DNA polymerase (5 U/µl) (Perkin-Elmer Corp.), and water to a final volume of 100 µl. In all PCR experiments these parameters were used and the number of reaction cycles was varied. References for the general use of PCR techniques include Mullis et al, Cold Spring Harbor Symp. Quant. Biol., 51:263, (1987), Ehrlich (ed), PCR technology, Stockton Press, New York, 1989, Ehrlich et al, Science, 252:1643–1650, (1991), "PCR protocols; A Guide to Methods and Applications", Eds. Innis et al, Academic Press, New York, (1990).

Sequencing

All constructs have been sequenced by the use of a Taq Dyedeoxy™ Terminator Cycle Sequencing Kit. The sequencing was performed on a ABI Prism 373 DNA Sequencer.

Agarose Electrophoresis

Figure 5:
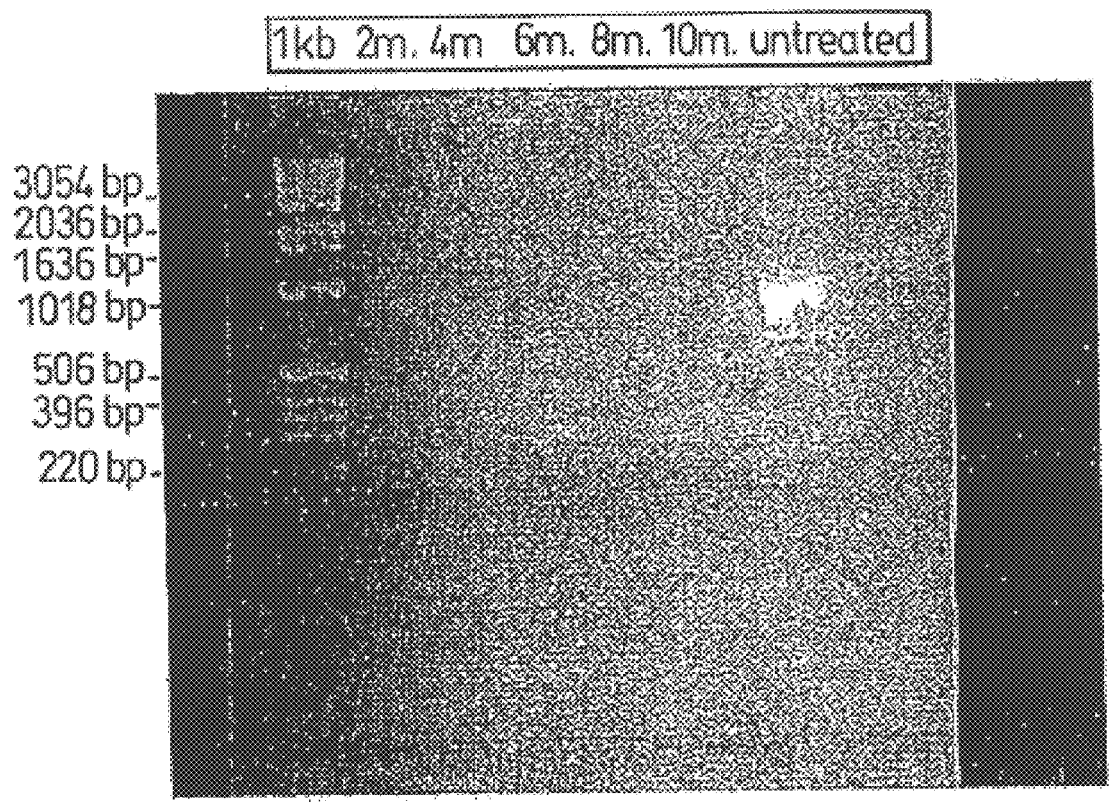
FIG. 5 shows the appearance of DNA at different fixed time intervals after digestion with BAL31 Nuclease. The DNA was mixed with the enzyme and incubated at 30° C. At different time points samples were removed and the enzymatic activity stopped by addition of 20 mM EGTA. The samples from the different time points were purified and analyzed on a 2% agarose gel. The samples are indicated as follows: 1 Kb=DNA molecular marker 1; 2–10 m=2 to 10 minutes BAL31 incubation samples.

Agarose electrophoresis of DNA was performed with 2% agarose gels composed of 1% NuSieve® GTG® Low Melting AGAROSE (FMC Bioproducts, Rockland, Me., USA) and 1% AMRESCO® Agarose (AMRESCO, SOLON, Ohio, USA) with 0.25 µg/ml ethidium bromide in Tris-acetate buffer (TAE-buffer 0.04M Tris-acetate, 0.001M EDTA). Samples for electrophoresis were mixed with a sterile filtrated loading buffer composed of 25% Ficoll and Bromphenolic blue and loaded into wells in a the 2% agarose gel. The electrophoresis was run at 90 V for 45 minutes unless otherwise stated in Tris-acetate buffer with 0.25 µg/ml ethidium bromide. Bands of appropriate size were gel-purified using the Qiaquick Gel Extraction Kit (Qiagen GmbH, Hilden, Germany). As molecular weight standard, DNA molecular weight marker 1 (Boehringer Mannheim GmbH, Germany) was used. The DNA-concentration of the gel extracted products were estimated using a spectrophotometer (see FIG. 5).

Bacterial Strains

The *Escherichia coli*-strain *E.coli* BMH71-18 (supE thi Δ(lac-proAB) F' [proAB⁺ lacI^q Δ(lacZ)M15]), was used as a bacterial host for transformations. Chemically competent cells of this strain were produced basically as described Hanahan, D. 1983. Studies on transformation of *Escherichia coli* with plasmids. J. Mol. Biol. 166: 557–580. Electrocompetent cells of this bacterial strain were produced (Dower, W. J., J. F. Miller, and C. W. Ragsdale. 1988: High efficiency transformation of *E.coli* by high voltage electroporation. Nucleic Acids Res. 16:6127).

Plasmids

The tetracycline resistance-gene of pBR322 is 1191 bp (basepairs) long. A deleted tetracycline resistance-gene variant of plasmid pBR322 was constructed by cleaving the plasmid with the restriction enzymes SalI and BamHI. This resulted in removal of a 276 bp fragment inside the tetracycline gene. A cleavage reaction with HindIII and EagI and the deleted plasmid would theoretically lead to a 634 bp cleavage-product, whereas a wildtype pBR322 cleaved with these enzymes produces a 910 bp product. The resulting protruding single stranded overhangs on the deleted plasmid after cleavage were treated with Klenow enzyme to generate double-stranded ends at both ends of the plasmid. These ends were then blunt-end ligated according to Molecular cloning; A LABORATORY MANUAL (Second Edition, Cold Spring Harbor Laboratory Press, 1989). The resulting plasmid was transformed into chemically competent *E.coli* BMH71-18 and plated onto ampillicin-containing plates (100 µg/ml). When replated onto tetracycline-containing agarplates (10 µg/ml) the colonies were tetracycline sensitive.

External Primers

Two external primers surrounding the tetracycline gene of pBR322 were designed with the following sequences including designated unique restriction sites:

pBR322 HindIII forward primer:
5'-CAGCTTATCATCGATAAGCTTTAATGCGGTAGTT TAT-3' (SEQ ID #1)

and pBR322-EagI-reversed-primer:
5'-CGTAGCCCAGCGCGTCGGCCGCCATGCCGGCG ATAATG-3' (SEQ ID #2)

To show that the two external primers covers the functional parts of the tetracycline-gene, a PCR reaction with the above mentioned profile was used for a 30 cycles-PCR with pBR322 (250 ng) as a template and the external primers described above. This yielded a PCR-product of 910 bp after subsequent cleavage with HindIII and EagI. When this restriction product was cloned in a likewise restriction-digested pBR322 plasmid, the plasmid encoded a tetracycline resistant phenotype. This was detected after transformation of a ligation of plasmid and 910 bp PCR-product into *E.coli* host BMH 7118 plated on tetracycline containing agar-plates (10 µg/ml).

STOP-containing Primers

Two pBR322 forward mutagenic primers and two pBR322 reversed primers containing unique restriction-sites and one STOP codon each at various sites were constructed. These were:

pBR322 NheI forward STOP:
5'-CACTATGGCGTGCTGCTAGCGCTATATGCGTTGAT GCAATTTCTATGAGCACCCGTTCT-3'. (SEQ ID #3)

pBR322 SalI reversed STOP:
5'-TCTCAAGGGCATCGGTCGACGCTCTCCCTTATG CGACTCCTGCATTAGGAATCAGCCCAGTAGTA-3' (SEQ ID #4)

Generation of STOP-codon Containing Variants of pBR322 Plasmids

Four different variants of the tetracycline gene were constructed. A combination of one mutated forward or reversed primer with the corresponding external forward or reversed primer was used in PCR-reactions to generate mutated inserts. Plasmid pBR322 was used as a template (250 ng) in 40 PCR-cycles. The resulting restriction digested fragments were then cloned into tetracycline deleted pBR322, and the resulting clones were called FIND 1 and FIND 3.

The following primer combinations were used: FIND 1, pBR322 NheI-forward-STOP-primer with pBR322-EagI-reversed-primer. This combination gave the insert after restriction digestion as shown in FIG. 6A; and FIND 3, pBR322 HindIII forward primer and pBR322 SalI reversed STOP primer. This combination gave the insert after restriction digestion as shown in FIG. 6B.

The amplified PCR-products were analysed on a 2% agarose gel. The electrophoresis was run at 90V for 40 minutes as described above. Bands of appropriate size (1000 bp), as compared to the molecular weight standard, were cut out and gel-purified using the Qiaquick Gel Extraction Kit. The four different STOP-containing inserts were then cleaved with the restriction-enzymes designated in the primers above. For each insert a pool of plasmid pBR322 was cleaved with the same enzymes, and these four combinations were then ligated and transformed into chemically competent E coli BMH 71-18 according to the modified protocol of Detlef (Modified Hanahan, revised M. Scott, F. Hochstenbach and D. Güssow 1989). The transformants were plated onto ampicillin containing agar-plates (50 μg/ml). When replated on tetracycline containing agar-plates (10 μg/ml) no colonies survived, confirming the functional effect of the introduced STOP-codon in the tetracycline-gene. Plasmids of the four different FIND-clones were prepared with Qiagen Plasmid Midi Kit (Qiagen Inc., Chatsworth, Calif., USA). The plasmids of the four clones were sequenced by the use of a Taq Dyedeoxy™ Terminator Cycle Sequencing Kit. The sequencing was performed on a ABI Prism 373 DNA Sequencer. The STOP-codons were confirmed and the inserts to be correct.

FIND Experiment I

Generation of FIND-fragments for BAL31 Nuclease Digestion

PCR-fragment of FIND 1 and FIND 3 were generated by running PCR-reactions with FIND 1 and FIND 3-plasmids as templates (500 ng) and with the two external primers, pBR322 HindIII forward primer and pBR322-EagI-reversed-primer. PCR-cycles were as described above for 30 cycles. The amplified PCR-products were mixed with 20 μl of loading buffer (25% Ficoll and Bromphenolic blue) and analysed on a 2% agarose gel. The electrophoresis was run at 90V for 35 minutes as previously described. Bands of appropriate size were cut out and gel-purified using the Qiaquick Gel Extraction Kit. The DNA-concentration was estimated to 112.25 μg/ml for the FIND-1 PCR-fragment and to 110 μg/ml for the FIND-3 PCR-fragment.

BAL31 Nuclease Treatment

5 μg each of FIND 1 and FIND 3 PCR-fragments (FIGS. 7 A and B) were mixed in equimolar amounts together with 100 μl of 2×BAL31 buffer and 10 μl sterile water to a final volume of 200 μl. A smaller volume of 22.5 μl was prepared to be used as an enzymatically untreated blank. This consisted of 4.5 μl FIND 1-fragment and 4.5 μl of FIND 3, 11.25 μl 2×BAL31 nuclease buffer and 2.25 μl sterile water. 1.5 ml sterile eppendorf tubes with DNA and 2×BAL31 nuclease buffer and water as described were pre-incubated in a 30° C. water-bath in a cold-room of +4° C. for 10 minutes. Meanwhile five sterile eppendorf tubes were prepared with 4 μl each of a 200 mM solution of EGTA. These were marked 1–9 minutes. In the same way a tube with 2.5 μl 200 mM EGTA was prepared for the blank untreated DNA-solution. The working concentration of EGTA is 20 mM. After the 10 minutes pre-incubation BAL31 Nuclease was added to the tube with the larger volume to a final concentration of 1 Unit/μg of DNA (10 μl of 1 U/μl solution). After t=1, 3, 5, 7 and 9 minutes the tube was mixed and samples of 36 μl was removed and added to the tubes with 4 μl of EGTA and placed onto ice. At the same time the blank volume of 22.5 μl was removed and added to the prepared 2.5 μl of EGTA and also placed on ice. The tubes were then placed in a 65° C. water-bath for heat inactivation of the enzyme and then replaced onto ice.

Purification of Digestion Produced Fragments

The volumes in the tubes were corrected to 100μl each and a phenol/chloroform/isoamylalcohol extraction was performed. 50 μl of buffered phenol was added to each tube together with 50 μl of a mixture of chloroform and isoamylalcohol (24:1). The tubes were vortexed for 30 seconds and then centrifuged for 1 minute in a microfuge at 14000 r.p.m. The upper phase was then collected and mixed with 2.5 volumes of 99.5% Ethanol (1/10 was 3M Sodium Acetate, pH 5.2). The DNA was precipitated for 1 hour in −80° C. The DNA was then pelleted by centrifugation for 30 minutes in a microfuge at 14.000 r.p.m. The pellet was washed once with 70% ethanol and then re-dissolved in 10 μl of sterile water.

Analysis of Digestion Produced Purified Fragments on Agarose Gel

5 μl of the dissolved pellet from each time point and from the blank were mixed with 2.5 μl of loading buffer (25% Ficoll and Bromphenolic blue) and loaded into wells in a 2% agarose gel. The electrophoresis and subsequent gel extraction of the different timepoints were performed as above.

Reassembly PCR with BAL31 Nuclease Generated Fragments

The remaining 5 μl of the dissolved pellet from each time point after phenol-extraction and precipitation were mixed in a PCR-reassembly without primers. A portion of 5 μl from the untreated blank was added as template to make it possible to generate full length fragments. 40 PCR-cycles were run with the PCR-profile and reaction mixture as described above, but without any primers.

PCR with External Primers to Increase the Amount of Reassembled PCR-products

50 μl of the reassembled PCR-product was mixed with PCR reagents including the two external primers as described above to generate a 100 μl PCR reaction. This PCR was run for 25 cycles with the profile described above. The amplified PCR-product was analysed on a agarose gel. A band of approximately 1000 bp was visible on the gel after the second PCR with the two external primers. The remaining 50 μl from the first reassembly PCR, showed only a smear of bands spanning the whole interval of the molecular weight marker. The 1000-bp fragment after the second PCR was excised and gel-purified as described previously.

Restriction Digestion of Reassembled FIND-fragment and Tetracycline Sensitive pBR322 with HindIII and EagI 10 μg of tetracycline deleted pBR322 (10 μl) was cleaved with 2 μl each of the enzymes HindIII (10 U/μl) and EagI (10 U/μl) (4 U enzyme/μg vector) in a mixture with 10 μl 10×buffer B (supplied with the enzymes) and water to 100 μl. All of the agarose purified reassembled FIND-fragment was cleaved with the same enzymes in a similar 100 μl reaction mixture. The tubes were incubated in a 37° C. water bath for 14 hours.

Gel Purification of Restriction Digested Vector and Restriction Digested Reassembled FIND-fragment The cleavage reactions were mixed were analysed on a 2% agarose gel. The restriction digested tetracycline-deleted pBR322 showed a cleavage product of about 600 bp. This corresponds well with the expected size of 635 bp. The band of the cleaved plasmid was cut out and gel-extracted as previously described. The reassembled cleaved FIND-product was about 1000 bp long and was gel extracted in the same manner as the plasmid.

Spectrophotometer estimations of the restriction digested-plasmid and FIND-fragment gave the following indications of DNA-concentrations: plasmid 13.5 μg/ml; reassembled cleaved FIND-fragment 77.3 μg/ml.

Ligation of Reassembled Restriction Digested FIND-fragment with Tetracycline Deleted Restriction Digested pBR322

9.6 μg of purificated cleaved tetracyclineresistance gene-deleted pBR322 was ligated to 2.76 μg purified reassembled restriction digested FIND-fragment at 12° C. water bath for 16 hours. 50 μl of the vector was mixed with 60 μl of the insert and 15 μl of 10×buffer (supplied with the enzyme) 7.5 μl ligase (5 U/μl) and sterile water to a final volume of 150 μl. A ligation of 2 μg restriction digested tetracyclineresistance gene-deleted pBR322 without any insert was also performed in the same manner.

Transformation of Chemically Competent E coli BMH 71-18 with the Ligated Reassembled FIND-insert and pBR322

The ligation reactions were purified by phenol/chloroform extraction as described above. The upper phase from the extraction was collected and mixed with 2.5 volumes of 99.5% Ethanol (1/10 was 3M Sodium Acetate, pH 5.2). The DNA was precipitated for 1 hour in −80° C. The DNA was then pelleted by centrifugation for 30 minutes in a microfuge at 14.000 r.p.m. The pellet was washed once with 70% ethanol and then re-dissolved in 10 μl of sterile water. 5 μl of each ligation was separately mixed with 95l chemically competent E coli BMH 71-18 incubated on ice for 1 hour and then transformed accordingly to the modified protocol of Detlef (Modified Hanahan, revised M. Scott, F. Hochstenbach and D. Güssow 1989). After one hour's growth the bacteria from the two transformations were spread onto ampicillin containing agar plates (100 μg/ml). The plates were grown upside-down in a 37° C. incubator for 14 hours.

Testing of Ampicillin-resistant Transformant for Tetracycline-resistant Recombinants The transformation with reassembled FIND-fragment and tetracycline-deleted pBR322 gave 122 ampicillin-resistant transformants. The religated cleaved empty tetracycline-deleted pBR322 gave 100 transformants. The transformants from both categories were transferred with sterile picks one at a time to tetracycline (10 μg/ml) containing agar plates and to ampicillin containing plates at the same time and to corresponding locations. These plates were incubated in 37° C. incubator for 14 hours.

Counting of Tetracycline Resistant Recombinants

The colonies on both the tetracycline plates and the ampicillin plates were counted the following day for both transformants.

FIND Experiment II

The above described methods were used for a second BAL31 Nuclease treatment with a mixture of 5 μg of FIND 1 and 5 μg of FIND 3 as described above and in the overview in FIG. 1. This time new PCR-fragments had been generated with the estimated concentrations of 192.25 μg/ml for FIND 1 and 231.5 μg/ml for FIND 3. The following reaction micture was used: 26 μl FIND 1, 21.6 μl FIND 3, 100 μl 2×BAL31 exonulease buffer, 9.9 μl BAL31 Nuclease and water to 200 μl. A blank was also prepared with 13 μl FIND 1 and 10.8 μl FIND 3, 36 μl 2×BAL31 exonulease buffer, 0 μl BAL31 Nuclease and water to 72 μl.

The BAL31 digestion was performed as described in the previous experiment and samples were withdrawn at the same timepoints to tubes with 200 mM EGTA to get a final concentration of 20 mM EGTA. The exonuclease in the resulting samples was heat-inactivated as described above and the fragments where extracted, precipitated and 50% were loaded on agarose gel. After the same appearance as previously on the gel had been established, the samples were purified and 2 sequential PCR-reactions were run as before. The final PCR-fragment was cloned into tetracycline deleted pBR322 under the same conditions as above. The ligation was then electroporated into electrocompetent cells as described (Dower, W. J., J. F. Miller, and C. W. Ragsdale. 1988: High efficiency transformation of E.coli by high voltage electroporation. Nucleic Acids Res. 16:6127.) and plated on ampicillin agar plates as before. Several thousands of transformants were achieved. 397 of these were transported as described above to tetracycline agar plates and ampicillin agar plates at the same time. The amount of tetracycline revertants were counted the following day after incubation in a 37° C. incubator for 14 hours.

The tetracyclin recombinants were then plated for separate colonies onto new tetracyclin plates. Separate colonies were then inoculated into liquid cultures with 1×TB-media (Terrific Broth; Molecular cloning; A LABORATORY MANUAL, Second Edition, Cold Spring Harbor Laboratory Press, 1989) with 1% Glucose and both ampicillin and tetracycline with the above concentrations and grown for plasmid-preparations with Qiagen Plasmid Midi Kit (Qiagen Inc., Chatsworth, Calif., USA). Glycerol stocks of these overnight cultures were prepared by mixing 500 μl of bacterial culture with 215 μl of 50% Glycerol and storing these mixtures at −80° C.

A bacterial PCR-screening with the two external primers mentioned above of 40 of the tetracycline-sensitive colonies was performed to estimate the frequency of empty religated vector among these transformants. This was done with the PCR-mixture mentioned previously scaled down to 25 μl reactions. These were inoculated with one sensitive bacterial colony each and the PCR-profile was as above for 30 cycles. The resulting PCR-fragmnets were analysed on gel as described above.

| FIND-experiment I: | |
|---|---|
| No. of amp.-resistant FIND-transformants | No. of tet-resistant FIND-transformants |
| 122 | 19 |
| Frequency of recombinants: 16% | |
| No. of amp.-resistant relig. sensitive vector | No. of tet.-resistant relig., Vect. |
| 100 | 0 |
| Frequency of recombinants: 0% | |
| FIND-experiment II: | |
| No. of amp.-resistant FIND-transformants | No. of tet-resistant FIND-transformants |
| 397 | 22 |

Frequency of recombinants: 5.5%

2 out of 40 bacterially PCR-screened sensitive clones were empty religated vector. This would then make up 5% of the total number of transformants. Therefore, 20 out of 397 is empty vector. This increased the number of recombinants to 5.8%.

FIND Experiment III

The FIND procedure is not restricted to the usage on tetracycline genes, but can be applied to any type of genes encoding a protein or protein motif. This is exemplified by creating a new repetoir of antibody fragments with mutations evenly spread over the entire antibody variable genes after FIND treatment.

Single base pair mutations were introduced into the VL and VH-regions of the anti-FITC scFv antibody fragment B11 (Kobayashi et al., Biotechniques Sep. 23, 1997; (3):500–503) by the use of error prone PCR in accordance with Kuipers et al., (Nucleic Acids Res Aug. 25, 1991; 19(16):4558) except for a raise in the $MgCl_2$ concentration from 2 mM to 5 mM. This anti FITC scFv antibody fragment was constructed by the use of overlap extension PCR, and the overlap extension procedure has previously been used for the random combination of DNA variation (Söderlind et al. Gene Jul. 28, 1995; 160(2):269–272).

The mutated products were then subjected to controlled degradation with BAL31 exonuclease which can be used for removing nucleotides from the termini of double stranded DNA in a controlled manner. It is predominantly a 3' exonuclease (Sambrook et al., Sambrook, J., Fritsch E. F. and Mantiatis T. Molecular Cloning—a laboratory Manual Cold Spring Harbor Laboratory Press, 2nd edition, 1989) and removes mono nucleotides from both 3' termini of the two strands of linear DNA. In addition, it also acts as an endonuclease degrading the ss DNA generated by the exonuclease activity. Degradation is completely dependent on the presence of calcium and the reaction can be stopped at different stages by adding the calcium chelating agent EGTA. Bal31 works asynchronously on a pool of DNA molecules, generating a population of DNA of different sizes whose termini have been digested to various extents and whose single stranded DNA tails vary in length. DNA of interest is digested with BAL31 and samples are withdrawn at different times and placed in a solution with EGTA, which does not interfere with the activity of Taq polymerase. Thus, PCR based reassembly is possible directly after the digestion procedure. The average length of single-stranded tails created by digestion of linear ds DNA is dependent both on time of Bal31 treatment and the enzyme concentration. High enzyme concentrations of 2–5 U/ml yields an average of 5 nucleotides of ssDNA per terminus, whereas 0.1–0.2 U/ml can yield longer ssDNA.

After the treatment of BAL31, the pool of generated DNA fragments of varying sizes, which were reassembled as previously described into full length scFv genes. The resulting genes were cloned into the phagemid vector pEXmide5 and the resulting library size after transformation was 5.7× $10^4$ cfu/ug DNA.

Single clones from the library were sequenced to estimate the genetic variability in the library. The frequencies of mutations found, distributed over the 782 bp long VL-VH-region of the scFv antibody ranged from 1–56 (Table 1). This is a mutation rate ranging from 0.13% to 7.16%, whereas the mutation rate for error prone PCR has been reported to be 0.7% (Kuipers et al., Nucleic Acids Res Aug. 25, 1991; 19(16):4558). This result demonstrates the effect of recombining mutations in a set of genes, resulting in a varied gene population which can be used in selections/screening of proteins with new and altered functions.

Reagents

AmpliTaq® polymerase was purchased from Perkin-Elmer Corp., dNTPs from Boehringer Mannheim Biochemica (Mannheim, Germany), and BAL 31 Nuclease from New England Biolabs Inc. (Beverly, USA). All restriction enzymes were purchased from Boehringer Mannheim Biochemica (Mannheim, Germany). Ethidium bromide was purchased from Bio-Rad Laboratories (Bio-Rad Laboratories, Hercules, Calif., USA). T4 DNA Ligase was purchased from Boehringer Mannheim Biochemica (Mannheim, Germany).

Primers

All primers were designed and synthesised at the department with a Applied Biosystems 391 DNA-synthesiser. The restriction sites introduced in each primer are underlined.

Reamplification Primers

For error prone PCR and reamplification PCR after Bal31 Treatment

3'-primer DL:FITC-b11-VL3'-FLAG-SAL 1:

5'-CAA CTT TCT TGT CGA CTT TAT CAT CAT CAT CTT TAT AAT CAC CTA GGA CCG TCA GCT TGGT-3' (SEQ ID #10)

5'-primer DL:FITC B11-VH-5' Nco1:

5'-ACT CGC GGC CCA ACC GGC CAT GGC CGA GGT GCA GCT GTT GGA G-3' (SEQ ID #11)

Sequencing Primers

Sequencing reversed pEXmide 4: 5'-GGA GAG CCA CCG CCA CCC TAA C-3' (SEQ ID #12)

pUC/M 13 reversed primer: 5'-TCA CAC AGG AAA CAG CTA TGA C-3' (SEQ ID #13)

Plasmids pEXmide V: 4055 bp NcoI- and SalI-sites are marked with underline text is shown in FIG. 8.

Error Prone PCR

The error prone PCR reactions were carried out in a 10×buffer containing 500 mM NaCl, 100 mM Tris-HCl, pH 8.8, 5 mM $MgCl_2$ 100 µg gelatine (according to Kuipers et al Nucleic Acids Res. Aug. 25, 1991; 19 (16):4558) except for a raise in the $MgCl_2$ concentration from 2 mM to 5 mM). For each 100 µl reaction the following was mixed:

dATP 5 mM 5 µl dGTP 5 mM 5 µl dTTP 10 mM 10 µl dCTP 10 mM 10 µl

20 µM 3' primer 1.5 µl

20 µM 5'-primer 1.5 µl

10×Kuipers buffer 10 µl sterile mp $H_2O$ 46.3 µl

The template scFv FITC B11 in pEXmideV vector (24.5 ng/µl) was added at an amount of 42 ng. 10 µl of 10 mM $MnCl_2$ was added and the tube was checked that no precipitation of MnO2 occurred. At last 5 Units of Taq enzyme was added. The error prone PCR was run at the following temperatures for 25 cycles without a hot start: 94° C. 1', 45° C. 1', 72° C. 1', using a 1 second ramp time, followed by a rapid cooling to 4° C. The resulting product was an error proned insert over the scFv FITC of 782 bp. This insert was purified with Qiaqucik PCR purification kit, before BAL 31 Nuclease treatment.

BAL31 Treatment

Error proned purified insert of the FITC B11 was digested with 0.5 U BAL 31 enzyme/pg insert DNA. 1.5 ml sterile eppendorf tubes with DNA, 2×BAL31 Nuclease buffer and water were pre-incubated in 30° C. for 10 minutes. After this pre-incubation, BAL31 Nuclease was added except for one control tube to a final concentration of 0.5 Unit/pg of DNA. The control tube, thus, contained only DNA buffer and water. After t=2', 4', 6', 8' and finally 10 minutes, the tube was mixed and samples were removed and added to the tubes with EGTA and placed on ice. The working concentration of EGTA was 20 mM. At the same time the control volume was removed from the water bath and this sample was also mixed with EGTA and placed on ice. The tubes were then placed in a 65° C. water-bath for heat inactivation of the enzyme and then replaced onto ice.

Reassembly of BAL31 Generated Fragments

The reassembly of the generated fragment pools were performed as previously described in two subsequent PCR reactions. The first PCR reaction was performed without the addition of any external primers by mixing equal amounts of the different time pools in a standard PCR reaction. The PCR reaction was run at 40 cycles consisting of following profile: denaturation (94° C. for 1 minute), primer annealing (55° C. for 1 minute) and extension (72° C. for 1 minute) using a 1 second ramp time. The PCR reactions contained, unless otherwise noted, 5 µl of each primer (20 µM), 16 µl of a dNTP mixture (1.25 mM each of dTTP, dATP, dCTP and dGTP), 10 µl 10×reaction buffer supplied with the enzyme, 0.5 µl AmpliTaq® thermostable DNA polymerase (5 U/µl) (Perkin-Elmer Corp.) and water to a final volume of 100 µl.

The reassembled products were then reamplified with a PCR containing the 3'- and 5'-external primers to generate an insert of the correct size and thereby also introducing the restriction sites NcoI and SalI for cloning into the pEXmideV vector. The PCR reaction was run at 25 cycles consisting of following profile: denaturation (94° C. for 1 minute), primer annealing (55° C. for 1 minute) and extension (72° C. for 1 minute) using a 1 second ramp time. The PCR reactions contained, 5 µl of each primer (20 µM), 16 µl of a dNTP mixture (1.25 mM each of dTTP, dATP, dCTP and dGTP), 10 µl 10×reaction buffer supplied with the enzyme, 0.5 µl AmpliTaq® thermostable DNA polymerase (5 U/µl) (Perkin-Elmer Corp.) and water to a final volume of 100 µl. The subsequent insert was purified on a 2% agarose gel using the Qiaquick gel extraction kit (Kobayashi et al., Biotechniques Sep. 23, 1997; (3):500–503).

Cloning in the PEXMIDEV Phagmid Vector

The insert and vector were digested with the NcoI and SalI enzymes from Boehringer Mannheim. The insert was cleaved with 10 U enzyme/µg DNA and vector with 4 U/µg DNA. The insert was then gel purified as described previously and the vector was purified using the Microcon 100 micro concentrators (Amicon, Inc., Beverly, Mass. 01915, USA). The vector was then cleaved with a third enzyme, the Pst I enzyme, who's restriction site is located in between the first two enzymes. The vector was gel purified with the Qiaquick gel extraction kit (Qiagen GmbH, Hilden, Germany). Insert and purified vector were ligated with 25 U T4 DNA ligase/ug DNA (Boehringer Mannheim) at a vector to insert ratio of 590 ng vector to 240 ng insert (12:1 molar ratio) for 14 hours at 12° C. The ligation reactions were purified by phenol chloroform extraction and ethanol precipitation and subsequently transformed into electro competent Top 10 F' bacterial cells. The library size was determined to $5.7 \times 10^4$ cfu/ug DNA. Glycerol stocks were produced after transformation according to J. Engberg et al (Molecular Biotechnology Vol 6, 1996 p287–310) and stored at −20° C.

Sequencing

Separate colonies from the glycerol stock library were grown and plasmid preparations were performed with Promega Wizard Plus Minipreps DNA purification System (Promega, Madison, Wis. USA). The VL and VH insert of these plasmids were amplified with a PCR containing the 3'- and 5'-external primers to generate an insert of the correct size. These inserts were then sequenced with Big Dye Dyedeoxy™ Terminator Cycle Sequencing Kit. The sequencing was performed on a ABI Prism 377 DNA Sequencer.

TABLE 1

Number of mutations in the 782 bp long scFv sequences after FIND treatment

| Clone | Number of Mutations |
|-------|---------------------|
| 1     | 1                   |
| 2     | 5                   |
| 3     | 8                   |
| 4     | 23                  |
| 5     | 50                  |
| 6     | 56                  |
| 7     | 10                  |
| 8     | 26                  |
| 9     | 38                  |
| 10    | 18                  |

What is claimed is:

1. A method for generating at least one polynucleotide sequence from a parent polynucleotide sequence encoding at least one protein motif, comprising the steps of
   a) digesting the parent polynucleotide sequence with an exonuclease to generate a population of fragments;
   b) contacting said fragments with an undigested template polynucleotide sequence under annealing conditions;
   c) amplifying the fragments that anneal to the template in step b) to generate at least one polynucleotide sequence encoding at least one protein motif having altered characteristics as compared to the at least one protein motif encoded by said parent polynucleotide.

2. A method according to claim 1 wherein the parent polynucleotide is double-stranded and the method further comprises the step of generating single-stranded polynucleotide sequence from said double-stranded fragments prior to step b).

3. A method according to claim 1 wherein template polynucleotide sequence is the parent polynucleotide sequence.

4. A method for generating at least one polynucleotide sequence from a parent polynucleotide sequence encoding at least one protein motif, in which said polynucleotide sequence has altered sequence at its termini as compared to said parent polynucleotide sequence comprising the steps of
   (a) digesting said parent polynucleotide sequence with an exonuclease to generate a population of fragments;
   (b) contacting said fragments with an undigested template polynucleotide sequence which is a variant of said parent polynucleotide sequence, under annealing conditions;
   (c) amplifying the fragments that anneal to the template in step b) to generate at least one polynucleotide sequence encoding at least one protein motif encoded by said parent polynucleotide.

5. A method for generating at least one polynucleotide sequence from a parent polynucleotide sequence encoding at least one protein motif, in which said polynucleotide sequence has altered sequence at its center as compared to said parent polynucleotide sequence comprising the steps of
   (a) digesting a population of variant polynucleotide sequences with an exonuclease to generate a population of fragments;
   (b) contacting said fragments with said parent polynucleotide sequence under annealing conditions, said parent polynucleotide sequence being undigested;
   (c) amplifying the fragments that anneal to the parent in step b) to generate at least one polynucleotide sequence encoding at least one protein motif encoded by said parent polynucleotide.

6. A method according to claim 4 wherein the exonuclease is BAL31.

7. A method according to claim 4 wherein the parent polynucleotide sequence encodes an antibody or fragment thereof.

8. A method according to claim 1 wherein the parent polynucleotide sequence encodes an enzyme.

9. A method according to claim 4 further comprising the step of screening the at least one polynucleotide generated in step c) for desired characteristics.

10. A method according to claim 4 further comprising the step of expressing the at least one polynucleotide generated in step c) and screening the resulting polypeptide for desired characteristics.

11. A method for preparing a pharmaceutical composition which comprises, following the identification of a polynucleotide with desired characteristics by a method according to claim 1, adding said polynucleotide to a pharmaceutically acceptable carrier.

12. A method for preparing a pharmaceutical composition which comprises, following the identification of a polypeptide with desired characteristics by a method according to claim 8, adding said polypeptide to a pharmaceutically acceptable carrier.

13. A process which comprises, following the identification of a polynucleotide by a method of claim 1, the manufacture of that polynucleotide, in whole or in part, optionally in conjunction with additional polynucleotide sequence.

14. A process which comprises, following the identification of a polypeptide by a method according to claim 9, the manufacture of that polypeptide, in whole or in part, optionally in conjunction with additional polypeptides.

15. A process according to claim 14 wherein the polypeptide is an antibody or fragment thereof.

16. A process according to claim 14 wherein the polypeptide is an enzyme.

17. A method according to claim 5 further comprising the step of screening the at least one polynucleotide generated in the step c) for desired characteristics.

18. A method according to claim 5 further comprising the step of expressing the at least one polynucleotide generated in step c) and screening the resulting polypeptide for desired characteristics.

* * * * *